US010610850B2

(12) United States Patent
Locke et al.

(10) Patent No.: US 10,610,850 B2
(45) Date of Patent: *Apr. 7, 2020

(54) PLASMA DISCHARGE REACTOR WITH FLOWING LIQUID AND GAS

(71) Applicant: FLORIDA STATE UNIVERSITY RESEARCH FOUNDATION, INC., Tallahassee, FL (US)

(72) Inventors: Bruce R. Locke, Tallahassee, FL (US); Igor Alabugin, Tallahassee, FL (US); Robert Wandell, Tallahassee, FL (US); Kevin Hsieh, Tallahassee, FL (US); Stefan Bresch, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 174 days.

This patent is subject to a terminal disclaimer.

(21) Appl. No.: 15/837,823

(22) Filed: Dec. 11, 2017

(65) Prior Publication Data

US 2018/0099258 A1    Apr. 12, 2018

Related U.S. Application Data

(62) Division of application No. 14/213,068, filed on Mar. 14, 2014, now Pat. No. 9,861,950.

(Continued)

(51) Int. Cl.
*B01J 19/08* (2006.01)
*C07C 29/48* (2006.01)

(52) U.S. Cl.
CPC .............. *B01J 19/088* (2013.01); *C07C 29/48* (2013.01); *B01J 2219/0805* (2013.01);
(Continued)

(58) Field of Classification Search
CPC .............. B01J 19/088; B01J 2219/0805; B01J 2219/0845; B01J 2219/0869;
(Continued)

(56) References Cited

U.S. PATENT DOCUMENTS

| 1,708,126 A | 4/1929 | Esmarch |
| 2,045,343 A | 6/1936 | Darrah |

(Continued)

FOREIGN PATENT DOCUMENTS

| CA | 1069857 A | 1/1980 |
| GB | 787748 A | 12/1957 |

(Continued)

OTHER PUBLICATIONS

Bresch et al.: "Oxidized Derivatives of n-Hexane from a Water/Argon Continuous Flow Electrical Discharge Plasma Reactor", Plasma Chemistry and Plasma Processing, 35(6) (2015) 553-584.

(Continued)

*Primary Examiner* — Xiuyu Tai
(74) *Attorney, Agent, or Firm* — Fox Rothschild LLP

(57) ABSTRACT

The activation of the C—H bond using low temperature plasma with an inlet liquid stream such that value added products are formed effectively. An organic liquid (e.g., hexane which is immiscible with liquid water) is injected into a flowing gas (argon) stream followed by mixing with a liquid water stream. Thereafter, the mixture contacts a plasma region formed by a pulsed electric discharge. The plasma formed with the flowing liquid and gas between the two electrodes causes chemical reactions that generate various compounds.

10 Claims, 24 Drawing Sheets

Related U.S. Application Data

(60) Provisional application No. 61/784,149, filed on Mar. 14, 2013.

(52) U.S. Cl.
CPC .......... *B01J 2219/0845* (2013.01); *B01J 2219/0869* (2013.01); *B01J 2219/0884* (2013.01); *B01J 2219/0894* (2013.01)

(58) Field of Classification Search
CPC ........ B01J 2219/0884; B01J 2219/0894; B01J 2219/00182; B01J 2219/0809; B01J 2219/0822; B01J 2219/083; B01J 2219/0839; B01J 2219/0871; B01J 2219/0877; C05C 5/00; C07C 29/48; Y02E 60/364

See application file for complete search history.

(56) References Cited

U.S. PATENT DOCUMENTS

| | | |
|---|---|---|
| 3,205,162 A | 9/1965 | Maclean |
| 3,497,436 A | 2/1970 | Yates et al. |
| 4,141,715 A | 2/1979 | Wyse et al. |
| 4,297,123 A | 10/1981 | Wyse et al. |
| 4,456,512 A | 6/1984 | Bieler et al. |
| 4,926,001 A | 5/1990 | Alagy et al. |
| 6,228,266 B1 | 5/2001 | Shim |
| 6,909,505 B2 | 6/2005 | Lucas et al. |
| 6,923,890 B2 | 8/2005 | Ricatto et al. |
| 7,378,062 B2 | 5/2008 | Itatani et al. |
| 7,604,719 B2 | 10/2009 | Vanden Bussche et al. |
| 7,919,053 B2 | 4/2011 | Burlica et al. |
| 8,444,924 B2 | 5/2013 | Burlica et al. |
| 2004/0116752 A1 | 6/2004 | Giapis et al. |
| 2006/0060464 A1 | 3/2006 | Chang |
| 2007/0167638 A1 | 7/2007 | Brophy et al. |
| 2008/0286169 A1 | 11/2008 | Meillot et al. |
| 2009/0004074 A1 | 1/2009 | Tonkovich et al. |
| 2009/0297406 A1 | 12/2009 | Okino et al. |
| 2010/0220182 A1 | 9/2010 | Krull et al. |
| 2011/0026657 A1 | 2/2011 | Laberge et al. |
| 2012/0000787 A1 | 1/2012 | Santilli |
| 2016/0102025 A1 | 4/2016 | Nunnally et al. |

FOREIGN PATENT DOCUMENTS

| | | |
|---|---|---|
| GB | 896113 A | 5/1962 |
| GB | 966406 A | 8/1964 |
| WO | 2012126095 A1 | 9/2012 |
| WO | 2013052548 A2 | 4/2013 |

OTHER PUBLICATIONS

Hsieh et al.: "Analysis of a gas-liquid film plasma reactor for organic compound oxidation", Journal of Hazardous Materials 317 (2016) 188-197.
Hsieh et al.: "Analysis of hydroxyl radical formation in a gas-liquid electrical discharge plasma reactor utilizing liquid and gaseous radical scavengers", Plasma Processes and Polymers, 14(8) e1600171 (2017).
Ammary, "Nutrients requirements in biological industrial wastewater treatment", African Journal of Biotechnology vol. 3 (4), pp. 236-238, Apr. 2004.
Yang et al.: "Occurrences and removal of pharmaceuticals and personal care products (PPCPs) in drinking water and water/sewage treatment plants: A review", Science of the Total Environment 596-597 (2017) 303-320.
Edward Archer et al.: "The fate of pharmaceuticals and personal care products (PPCPs), endocrine disrupting contaminants (EDCs), metabolites and illicit drugs in a WWTW and environmental waters", Chemosphere 174 (2017) 437-446.
Deblonde T, Cossu-Leguille C and Hartemann P 2011 Emerging pollutants in wastewater: A review of the literature International Journal of Hygiene and Environmental Health 214 442-8.
Geissen et al.: 2015 Emerging pollutants in the environment: A challenge for water resource management International Soil and Water Conservation Research 3 57-65.
Fujii et al.: 2007 New POPs in the water environment: distribution, bioaccumulation and treatment of perfluorinated compounds—a review paper Journal of Water Supply Research and Technology—Aqua 56 313-26.
Esler, "Concerning Recalcitrant/Refractory Organic Species and Chemical Oxygen Demand (COD) analysis by two different methods: (a) CODCr (the dichromate method) and (b) TiO2/UV photoelectrochemistry (the PeCOD™ method)", Aqua Diagnostic 2008.
Montes-Grajales D et al.: "Occurrence of personal care products as emerging chemicals of concern in water resources: A review" 2017 Science of the Total Environment 595 601-14.
Mompelat S et al. "Occurrence and fate of pharmaceutical products and by-products, from resource to drinking water" 2009 Environment International 35 803-14.
Macedo S et al.: "Methyl-triclosan and triclosan impact embryonic development of Danio rerio and Paracentrotus lividus" 2017 Ecotoxicology 26 482-9.
Khetan S K et al.: "Human pharmaceuticals in the aquatic environment: A challenge to green chemistry Chemical Reviews" 2007 107 2319-64.
Mora et al., "Selectivity control in a microwave surface-wave plasma reactor for hydrocarbon conversion", Plasma Processes and Polymers (2011) 8: 709-717.
Nozaki et al., "A single step methane conversion into synthetic fuels using microplasma reactor", Chemical Engineering Journal (2011) 166: 288-293.
Nozaki et al., "Innovative methane conversion technology using atmospheric pressure non-thermal plasma", Journal of the Japan Petroleum Institute (2011) 54: 146-158.
Nozaki et al., "Micro-plasma technology—direct methaneto-m ethanol in extremely confined environment", Natural Gas Conversion VII (2004) 147: 505-510.
Nozaki et al., "Partial oxidation of methane using microscale non-equilibrium plasma reactor", Catalysis Today (2004) 98: 607-616.
Nozaki et al., "Selective conversion of methane to synthetic fuels using dielectric barrier discharge contacting liquid film", Journal of Physics D—Applied Physics (2011) 44.
Okazaki et al., "Direct conversion from methane to methanol for high efficiency energy system with exergy regeneration", Energy Conversion and Management (2002) 43: 1459-1468.
Patino et al., "Oxidation of cycloalkanes and diesel fuels by means of oxygen low pressure plasmas", Energy & Fuels (2002) 16: 1470-1475.
Patino et al., "Upgrading of diesel fuels and mixtures of hydrocarbons by means of oxygen low pressure plasmas: A comparative study", Fuel (2003) 82:1613-1619.
Perevezentsev et al., "Transformations of benzene-argon mixture in barrier discharge", High Energy Chemistry (2011) 45: 62-65.
Prieto et al., "Nonthermal plasma reactors for the production of light hydrocarbon olefins from heavy oil", Brazilian Journal of Chemical Engineering (2003) 20: 57-61.
Prieto et al., "Reforming of heavy oil using nonthermal plasma", IEEE Transaction on Industry Applications (2001) 37: 1464-1467.
Rasmussen et al., "Direct partial oxidation of natural gas to liquid chemicals: Chemical kinetic modeling and global optimization", Industrial & Engineering Chemistry Research (2008) 47: 6579-6588.
Sedelmeier et al., "KMnO4-mediation oxidation as a continuous flow process", Organic Letters (2010) 12: 3618-3621.
Sekiguchi et al., "Direct hydroxylation of benzene using micro plasma reactor", Kagaku Kogaku Ronbunshu (2004) 30: 183-185. (abstract translation).
Shul'Pin et al., "Alkane oxygenation with H2O2 catalysed by FECI3 and 2,2'-bipyridine", Tectrahedron Letters (2005) 46: 4563-4567.

(56) References Cited

OTHER PUBLICATIONS

Sivaramakrishnan et al., "Rate constants for OH with selected large alkanes: Shock-tube measurements and an improved group scheme", Journal of Physical Chemistry A (2009) 113: 5047-5060.
Sprengnether et al., "Rate constants of nine C6-C9 alkanes with OH from 230 to 379 K: Chemical tracers for OH", Journal of Physical Chemistry A (2009) 113: 5030-5038.
Sugai et al., "Improvement of efficiency for decomposition of organic compounds in water using pulsed streamer discharge in air with water droplets by increasing residence time", Pulsed Power Conference (2009): 1056-1060.
Suhr et al., "Organic syntheses under plasma conditions", Pure and Applied Chemistry (1974) 39: 395-414.
Suss-Fink et al., "Alkane oxidation with hydrogen peroxide catalyzed homogeneously by vanadium-containing polyphosphomolybdates", Applied Catalysis A—General (2001) 217: 111-117.
Suzuki et al., "Investigation of a pulse circuit design and pulse condition for the high energy efficiency on water treatment using pulsed power discharge in a water droplet spray", IEEE Transactions on Dielectrics and Electrical Insulation (2011) 18: 1281-1286.
Takale et al., "Oxidation of dihydrazones of diarylacetylenes using sodium periodate", Chemistry Letters (2010) 39: 1279-1280.
Tezuka et al., "Oxidation of aromatic hydrocarbons with oxygen in a radiofrequency plasma", Plasma Chemistry and Plasma Processing (1996) 16:329-340.
Tezuka et al., "Oxidation of cycloalkanes in a radiofrequency plasma", Bulletin of Chemical Society of Japan (1991) 64: 1063-1065.
Thagard et al., "Electrical discharges in polar organic liquids", Plasma Processes and Polymers (2009) 6: 741-750.
Thornton et al., "Hydrazine synthesis in silent electrical discharge", Advances in Chemistry Series (1969): 165.
Thornton et al., "Hydrazine synthesis in silent electrical discharge", Nature (1967) 213: 1118.
Thornton et al., "Synthesis of formaldehyde from methane in electrical discharges", Nature (Feb. 11, 1967) 213: 590-591.
Sergio et al., "Synthesis of formaldehyde from methane and water in an electrical discharge 2-phase reactor", Journal of Applied Chemistry (1967) 17:325.
Wilson et al., "Measurement and estimation of rate constants for the reactions of hydroxyl radical with several alkanes and cycloalkanes", Journal of Physical Chemistry A (2006) 110: 3593-3604.
Yaji Ma et al., "Oxidation reactions of aromatic ethenes in solution exposed to low-temperature oxygen plasma", Journal of Photopolymer Science and Technology (2007) 20: 235-238.
Yamamoto et al., "Wet type plasma reactor for incinerator", Conference Record of the 1998 IEEE Industry Applications Conference (1998) 1-3: 1861-1864.
Jaramillo-Sierra et al, "Degradation of m-cresol in aqueous solution by dielectric barrier discharge," Journal of Physics; Conference Series 406 (2012) 012025.
Rumbach et al, "Decoupling Interfacial Reactions between Plasmas and Liquids: Charge Transfer vs Plasma Neutral Reactions," J. Am. Chem. Soc. 2013, 135, pp. 16264-16267.
Kuroki et al, "Decomposition of Trace Phenol in Solution Using Gas-Liquid Interface Discharge," Japanese J. of Appl. Phys. vol. 45, No. 5A, 2006, pp. 4296-4300.
Ognier et al, "Analysis of Mechanisms at the Plasma-Liquid Interface in a Gas-Liquid Discharge Reactor Used for Treatment of Polluted Water," Plasma Chem. Plasma Process (2009) 29:261-273.
Magureanu et al, "Degradation of pharmaceutical compound pentoxifylline in water by non-thermal plasma treatment," Water Research 44 (2010) pp. 3445-3453.
Magureanu et al, "Degradation of antibiotics in water by non-thermal plasma treatment," Water Research 45 (2011) pp. 3407-3416.
Lukes et al, "Hydrogen Peroxide and Ozone Formation in Hybrid Gas-Liquid Electrical Discharge Reactors," IEEE Trans. Ind. Appl., vol. 40, No. 1, Jan./Feb. 2004, pp. 60-67.
Locke et al, "Elementary Chemical and Physical Phenomena in Electrical Discharge Plasma in Gas-Liquid Environments and in Liquids," Ch. 6, pp. 185-241 of Plasma Chemistry and Catalysis in Gases and Liquids, 1st ed., Parvulescu et al eds., 2012.
International Search Report dated Jun. 9, 2015 in International Application No. PCT/US2015/020475.
Gubkin, "Electrolytische Metallabscheidung an der freien Oberflache einer Salzlosung" Ann. Physik (1887) 32: 114.2.
Niozaki et al., "Micro-plasma technology—direct methane to-methanol in extremely confined environment", Natural Gas Conversion VII (2004) 147: 505-510.
Agiral et al., "Gas-to-liquids process using multi-phase flow, non-thermal plasma microreactor", Chemical Engineering Journal (2011) 167: 560-566.
Akiyama, "Streamer discharges in liquids and their applications", IEEE Transactions on Dielectrics and Electrical Insulation (2000) 7: 646-653.
Bie et al., "Dielectric barriers discharges used for the conversion of greenhouse gases: Modeling the plasma chemistry by fluid simulations", Plasma Sources Science & Technology (2011) 20(2): 024008. (12 pages).
Bie et al., "Fluid modeling of the conversion of methane into higher hydrocarbons in an atmospheric pressure dielectric barrier discharge", Plasma Processes and Polymers (2011) 8: 1033-1058.
Bruggeman et al., "Non-thermal plasmas in and in contact with liquids", Journal of Physics D: Applied Physics (2009) 42: 1-28.
Burlica et al., "Formation of H2 and H2O2 in water-spray gliding arc nonthermal plasma reactor", Industrial & Engineering Chemistry Research (2010) 49(14): 6342-6349.
Burlica et al., "Hydrogen generation by pulsed gliding arc discharge plasma with sprays of alcohol solutions", Industrial & Engineering Chemistry Research (2011) 50: 9466-9470.
Burlica et al., "Pulsed plasma gliding arc discharges with water spray", IEEE Transactions on Industry Applications (2008) 44: 482-489.
Davies et al., "Glow-discharge electrolysis. Part I. The Anodic formation of hydrogen peroxide in inert electrolytes", Journal of the Chemical Society, Faraday Transactions (1952) Sept: 3595-3602.
Friedrich, "Mechanisms of plasma polymerization—Reviewed from a chemical point of view", Plasma Processes and Polymers (2011) 8: 783-802.
Gambus et al., "Oxidation of long chain hydrocarbons by means of low-pressure plasmas", Energy & Fuels (2001) 15: 881-886.
Gesser et al., "The direct conversion of methane to methanol by controlled oxidation", Chemical Reviews (1985) 85: 235-244.
Goujard et al., "Plasma-assisted partial oxidation of methane at low temperatures: Numerical analysis of gas-phase chemical mechanism", Journal of Physics D—Applied Physics (2011) 44(27): 274011. (13 pages).
Gubkin, "Electrolytische Metallabscheidung an der freien Oberflache einer Salzlosung" Ann. Physik (1887) 32: 114.
Hickling et al., "Contact glow-discharge electrolysis", Transactions of the Faraday Society (1964) 60: 783-793.
Hickling, "Electrochemical processes in glow discharge at the gas-solution interface", Modern Aspects of Electrochemistry (1971) 6: 329-373.
Hijikata et al., "Methanol conversion from methane and water vapor by electric discharge (effect of electric discharge process on methane conversion)", Heat Transfer Asian Research (1999) 28: 404-417.
Honorato et al., "(1)H low- and high-field NMR study of the effects of plasma treatment on the oil and water fractions in crude heavy oil", Fuel (2012) 92: 62-68.
Hsieh et al., "Optical diagnostics of electrical discharge water-spray reactors for chemical synthesis", IEEE Transactions on Industry Applications (2013) 49: 305-310.
Hueso et al., "Water plasmas for the revalorisation of heavy oils and cokes from petroleum refining", Environmental Science & Technology (2009) 43: 2557-2562.
Indarto, "A review of direct methane conversion to methanol by dielectric barrier discharge", IEEE Transactions on Dielectrics and Electrical Insulation (2008) 15: 1038-1043.

(56) References Cited

OTHER PUBLICATIONS

Jannini et al., "Hydrogen peroxide oxidation of alkanes catalyzed by the vanadate ion-pyrazine-2-carboxilic acid system", Petroleum Chemistry (2005) 45: 413-418.
Jia et al., "Catalytic functionalization of arenes and alkanes via C-H bond activation", Accounts of Chemical Research (2001) 34: 633-639.
Kamata et al., "Efficient stereo- and regioselective hydroxylation of alkanes catalysed by a bulky poloxometalate", Nature Chemistry (2010) 2: 478-483.
Khani et al., "Investigation of cracking by cylindrical dielectric barrier discharge reactor on the n-hexadecane as a model compound", IEEE Transactions on Plasma Science (2011) 39: 1807-1813.
Kobayashi et al., "The effect of spraying of water droplets and location of water droplets on the water treatment by pulsed discharge in air", IEEE Transactions on Plasma Science (2010) 38: 2675-2680.
Koslov et al., "The kinetics and mechanisms of cyclohexane oxygenation by hydrogen peroxide catalyzed by a binuclear iron complex", Russian Journal of Physical Chemistry (2003) 77: 575-579.
Kudryashov et al., "Oxidation of hydrocarbons in a barrier discharge reactor", High Energy Chemistry (2000) 34: 112-115.
Kudryashov et al., "Oxidation of hydrocarbons in a bubble plasma reactor", Petroleum Chemistry (2004) 44: 438-440.
Kudryashov et al., "Oxidation of propylene and isobutylene in a reactor with barrier discharge", Russian Journal of Applied Chemistry (2004) 77: 1904-1906.
Kudryashov et al., "Oxidation of propylene with air in barrier discharge in the presence of octane", Russian Journal of Applied Chemistry (2011) 84: 1404-1407.
Kudryashov et al., "Oxidative conversion of cyclohexane in discharge plasma maintained with different high-voltage power sources", High Energy Chemistry (2008) 42: 51-55.
Kudryashov et al., "Simulation of the kinetics of cyclohexane oxidation in a barrier discharge reactor", High Energy Chemistry (2002) 36: 349-353.
Kudryashov et al., "Study of the products of Benzene Transformation in the presence of argon, hydrogen, and propane-butane mixture in barrier discharge", Petroleum Chemistry (2012) 52: 60-64.
Kudryashov et al., "Transformations of n-hexane and cyclohexane by barrier discharge processing in inert gases", High Energy Chemistry (2001) 35: 120-122.
Labinger et al., "Understanding and exploiting C-H bond activation", Nature (2002) 417: 507-514.
Lee et al., "The characteristics of direct hydroxylation of benzene to phenol with molecular oxygen enhanced by pulse DC corona at atmospheric pressure", Plasma Chemistry and Plasma Processing (2003) 23: 519-539.
Locke et al., "Electrohydraulic discharge and nonthermal plasma for water treatment", Industrial & Engineering Chemistry Research (2006) 45:882-905.
Locke et al., "Elementary chemical and physical phenomena in electrical discharge plasma in gas-liquid environments and in liquids", Plasma Chemistry and Catalysis in Gases and Liquids (2012).
Locke et al., "Review of the methods to form hydrogen peroxide in electrical discharge plasma with liquid water", Plasma Sources Science and Technology (2011) 20: 034006.
Lukes et al., "Aqueous-phase chemistry of electrical discharge plasma in water and in gas-liquid environments", Plasma Chemistry and Catalysis in Gases and Liquids (2012) 1st ed. (ch. 7): 243-308.
Lukes et al., "Biological effects of electrical discharge plasma in water and in gas-liquid environments", Plasma Chemistry and Catalysis in Gases and Liquids (2012) 1st ed. (ch. 8): 309-352.
Malik et al., "Preliminary studies on formation of carbonaceous products by pulsed spark discharges in liquid hydrocarbons", Journal of Electrostatics (2008) 66: 574-577.
Malik et al., "Water purification by electrical discharges", Plasma Sources Science and Technology (2001) 10: 82-91.
Malik et al., "Water purification by plasmas: Which reactors are most energy efficient", Plasma Chemistry and Plasma Processing (2010) 30: 21-31.
Mandelli et al., "Hydrogen peroxide oxygenation of saturated and unsaturated hydrocarbons catalyzed by montmorillonite or aluminum oxide", Catalysis Letters (2009) 132: 235-243.
Monod et al., "Structure-activity relationship for the estimation of OH-oxidation rate constants of aliphatic organic compounds in the aqueous phase: Alkanes, alcohols, organic acids and bases", Atmospheric Environments (2008) 42: 7611-7622.

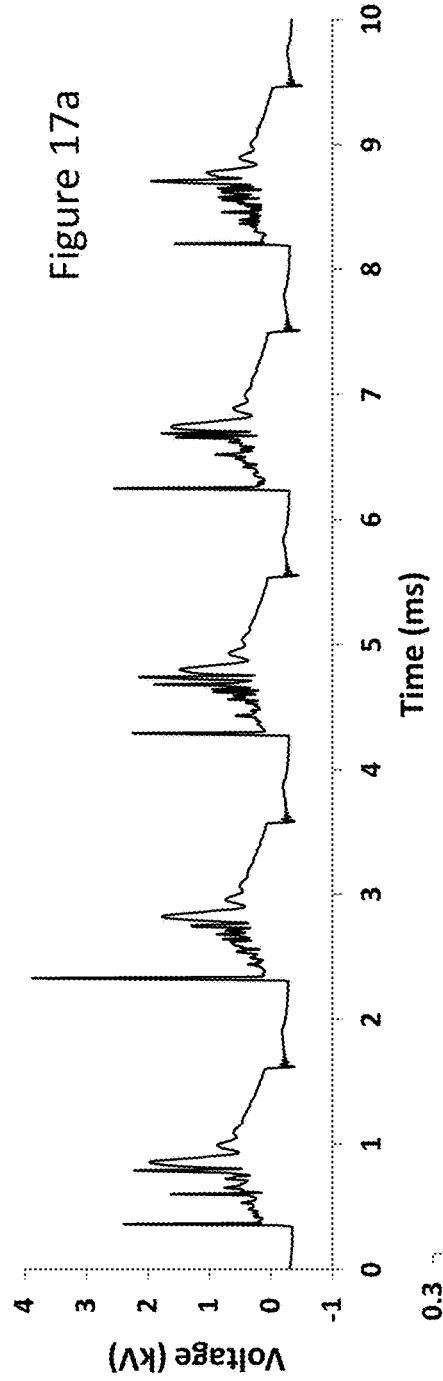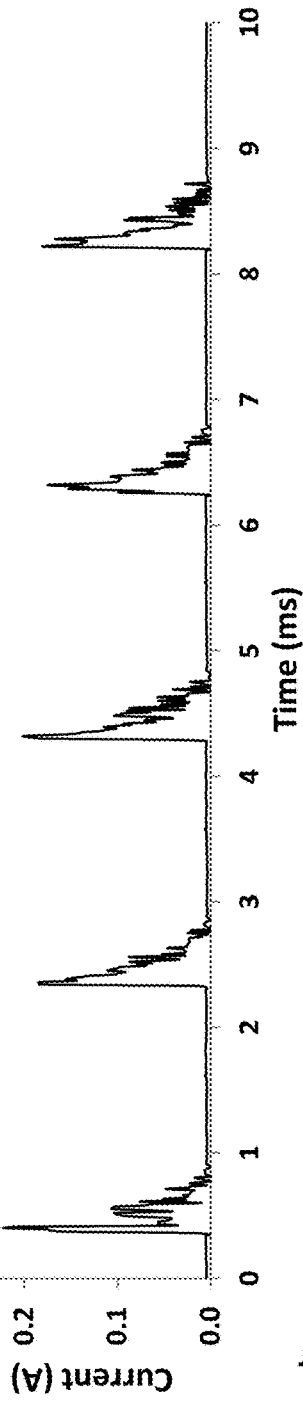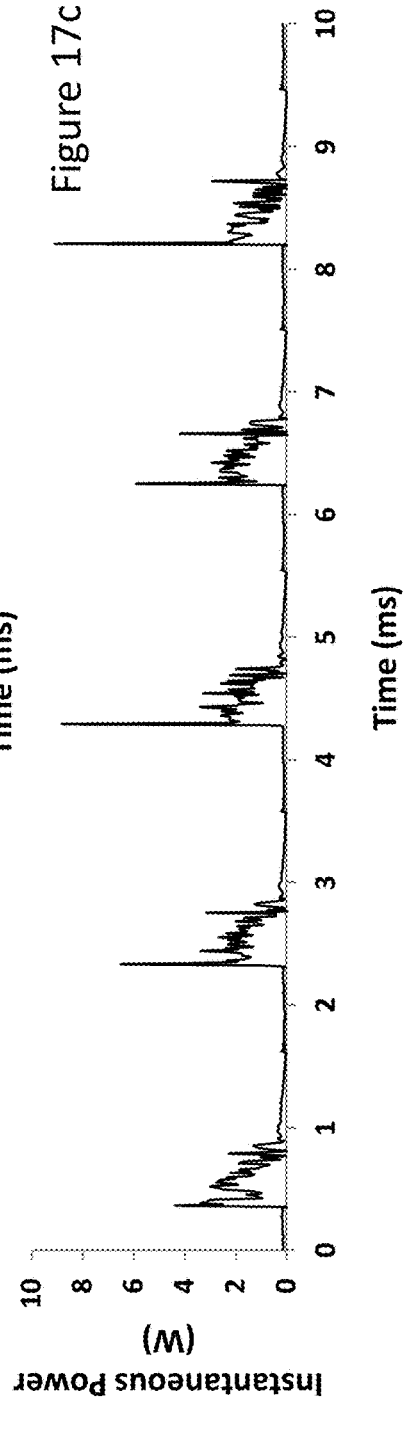

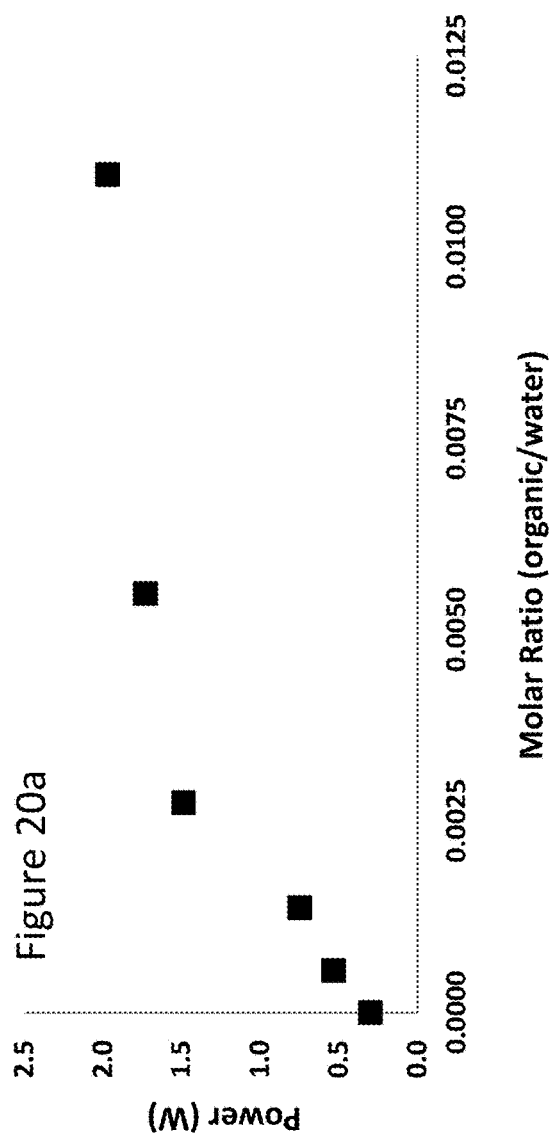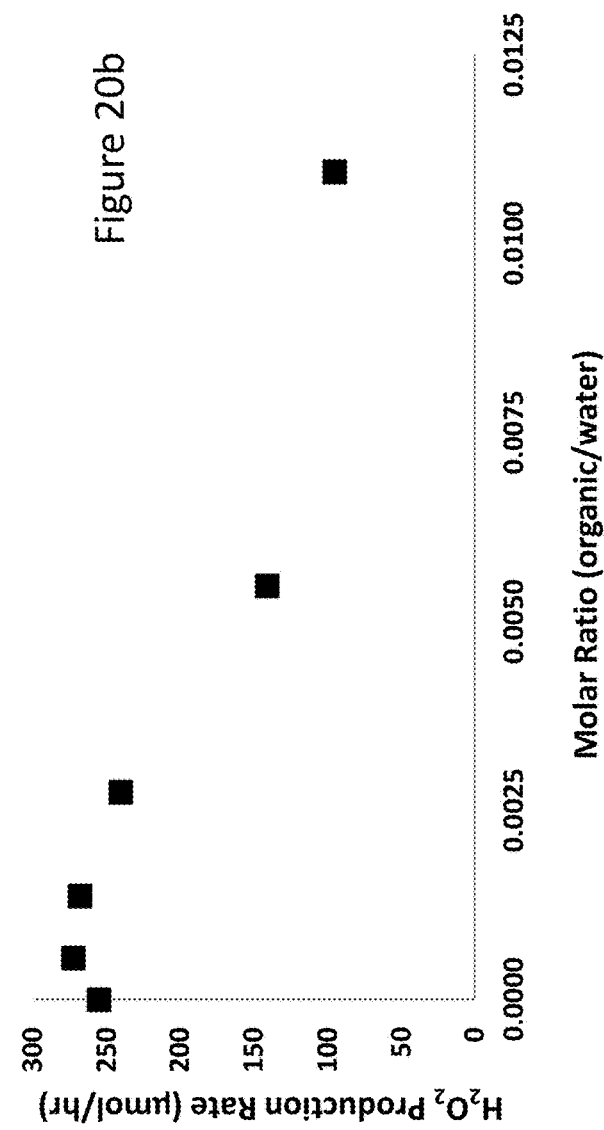

PLASMA DISCHARGE REACTOR WITH FLOWING LIQUID AND GAS

CROSS-REFERENCES TO RELATED APPLICATIONS

This application is a divisional of U.S. application Ser. No. 14/213,068 filed Mar. 14, 2014 which claims benefit under 35 U.S.C. § 119(e) to U.S. Provisional Patent Application Ser. No. 61/784,149, filed on Mar. 14, 2013, titled "Organic Chemical Synthesis Using Plasma Reactors With Liquid Organic and Liquid Water", which are hereby incorporated by reference in their entireties.

STATEMENT REGARDING FEDERALLY SPONSORED RESEARCH OR DEVELOPMENT

This invention was made with government support under Grant No. CBET 1236225 awarded by the National Science Foundation. The government has certain rights in this invention.

BACKGROUND OF THE INVENTION

1. Field of the Invention

The invention relates generally to activation of a C—H bond using a low temperature plasma and more specifically to activation of a C—H bond using a low temperature plasma and an inlet liquid stream.

2. Description of the Related Art

Electrical discharge plasma contacting liquid phases has been studied for a wide range of chemical, biomedical, environmental, and materials synthesis applications. The synthesis of a number of organic and inorganic compounds by gas-liquid plasma can involve glow discharge electrolysis whereby one electrode is placed inside the liquid phase and one in the gas phase. A wide range of other gas-liquid contacting schemes has been studied including falling films, aerosol sprays, and bubble injection into liquids. It has been shown that the presence of the liquid phase not only affects plasma properties such as electron energy and density, but also the chemical reactions which take place. The liquid phase can also serve as a source of additional vapor phase reactant as well as function as a reservoir to collect the generated products, protecting those products from degradation by direct electron attack in the gas phase plasma. Reactions with organic compounds in plasma discharges have been investigated for a wide range of applications and conditions including cases of plasma polymerization, plasma discharge in organic liquids, and the more commonly studied cases of organic compounds in liquid water for pollution control. Plasma generated directly in an organic liquid phase has been demonstrated to form diamond coatings and other carbonized materials such as nanofibers. Gas phase plasma (spark discharge: 3 to 12 W) generated with argon over heavy oils (n-$C_{10}$ to n-$C_{25}$ hydrocarbons) leads to significant chain breakage to form one to four carbon containing compounds with ethylene and hydrogen being the predominate species. Liquid n-hexadecane was studied as a model of a hydrocarbon oil and was cracked into $C_6$ to $C_{15}$ hydrocarbons using a dielectric barrier discharge with a methane carrier over the liquid hydrocarbon. In another example, crude oil was treated with a dielectric barrier discharge for various carrier gases ($H_2$, $CO_2$, $CH_4$) where rheological analysis showed a decrease in viscosity of the crude oil treated by plasma, and NMR analysis showed that the plasma treatment primarily led to water extraction from the naturally occurring emulsified water in the crude. Finally, an 80 W microwave plasma with water vapor over a heavy oil liquid demonstrated a series of reaction products from long chain aromatics to linear and shorter aromatic rings and, finally, syngas, $CO_2$ and small alkanes and alkenes, as well as traces of other carbonaceous products.

Previous studies have also demonstrated efficient production of $H_2$ from methanol and water/methanol mixtures, as well as other alcohol solutions, using a spray reactor. Clearly at high enough plasma power and exposure time, a wide range of hydrocarbons, even from heavy oils, can be cracked to relatively small compounds. The key issues that will make these types of applications useful for chemical synthesis of valuable products are to control or stop the plasma-induced radical reactions and to promote reaction selectivity. For example, some selectivity was demonstrated in a gas phase microwave plasma with n-hexane vapor in flowing argon through changes in the plasma input power, feed flow rates, and location of the feed.

Oxidation of the C—H group in alkanes under low temperature and pressure conditions is a significant challenge due to selectivity issues and over oxidation by harsh conditions. While catalysts have been developed that use hydrogen peroxide to form OH radicals capable of functionalizing alkanes, the reactions are quite complex. Hydrogen abstraction of alkanes at high temperature primarily for combustion has also been studied.

Plasma processes have been demonstrated to produce methanol from methane with high efficiency. Much of the extensive literature on methane conversion in plasma reactors focuses on methane conversion in dry gas to higher hydrocarbons and some effort has been devoted towards methane to methanol and/or formaldehyde conversion with water vapor and or liquid water films.

In plasma discharge in humid gas the direct conversion of methane to methanol can be expressed by Equation (1):

$$CH_4 + H_2O \rightarrow CH_3OH + H_2 \quad (1)$$

The conversion proceeds by the direct reaction of methyl radicals, $CH_3$, with hydroxyl radicals, OH. In addition to methanol, formaldehyde and formic acid are formed. Using a 500 Hz pulsed discharge reactor at approximately 400 degrees Celsius and relatively low pressure of 10 to 40 Torr, and power of 2 to 6 W, they found methanol yield of approximately 0.8% with energy yields of up to 10 g/kWh for glow-like discharge, but at high voltage spark-like discharge with lower power (5 mW) discharge they claim approximately 100 times better efficiency at 1 kg/kWh. While the yield is relatively small, the energy efficiency is high and may be economically competitive. The reaction kinetics of methane oxidation have been extensively studied and include the main reactions given by Equations (2)-(6):

$$CH_4 + OH \rightarrow CH_3 + H_2O \quad (2)$$

$$CH_3 + O_2(+M) \rightarrow CH_3OO(+M) \quad (3)$$

$$CH_3 + HO_2 \rightarrow CH_3O + OH \quad (4)$$

$$CH_3OO + CH_3 \rightarrow CH_3O + CH_3O \quad (5)$$

$$CH_3O + CH4 \rightarrow CH_3OH + CH_3 \quad (6)$$

As with the formation of hydrogen peroxide and hydrazine, the formation of methanol may be optimized under conditions where degradation reactions with radicals are minimized and over oxidation to CO and $CO_2$ is suppressed.

Alkanes and other compounds have been oxygenated by oxygen radicals in oxygen plasma as well. However, oxidation with hydroxyl radicals from liquid water in gas-liquid plasma systems has mostly been used to oxidize organic compounds in liquid water for pollution control. Reactions of alkanes such as n-hexane and cyclohexane with OH radicals produced from liquid water by plasma discharge where the plasma channels propagate along a gas-liquid interface have not, to our knowledge, been reported.

There are three important differences between the functionalization of hydrocarbons to produce small intermediate products by plasma and the more extensively studied plasma polymerization processes. In plasma polymerization, the desired goal is to form a surface polymer coating using gas phase plasma containing the precursor molecules. In such cases, a large conversion is required to form the coating. In order to produce a large conversion, a large plasma energy is required which leads to complete dissociation of the precursor compounds into small organic fragments. The resulting recombination reactions are not significantly selective due to the large number of possible reactions which can occur. One goal of the present work is to introduce selectivity. Although selectivity may come at the cost of lower conversion, this cost can be compensated in synthetic chemistry by component recirculation as well as series or parallel reactor designs. The second issue relates to the site of the main polymerization reactions. In plasma polymerization there is still debate on whether the main polymerization reactions occur in the gas phase or on the surface. Both cases are predicted to lead to the "irregular structure" of the polymer, where the reactor pressure and plasma pulsing can affect the location of these reactions. In gas-liquid plasma systems the physical location of the plasma chemical synthesis will depend, in part, on the volatility of the precursor molecule. Under conditions of low volatility, the plasma radicals may directly impinge on the liquid surface initiating reactions at the interface or even generate some radicals in the liquid phase. For high volatility cases, the organic liquid is fully vaporized and can react directly in the gas phase. Different product distributions are expected in these different conditions. A third issue relates to modification of reactor/reaction conditions involving generation of pulses by the power supply. Shorter plasma pulses (or with superimposed pressure pulses) have been shown to control chain propagation in plasma polymerization, but again at the cost of yield.

There is a need to utilize a pulsed plasma reactor with a flowing liquid water film, carrier gas, and various organic compounds for the synthesis of more chemical species.

BRIEF SUMMARY OF THE INVENTION

Various embodiments utilize a pulsed plasma reactor with a flowing liquid water film, carrier gas, and various organic compounds for the synthesis of more chemical species. The conversion of water into hydrogen peroxide and the normal alkane n-hexane and the cyclic alkane cyclohexane into oxygenated products (alcohols, ketones, and aldehydes) by hydroxyl radical attack was achieved. Reaction products were determined by GC-MS and NMR spectroscopy.

BRIEF DESCRIPTION OF THE DRAWINGS

These and other features, aspects, and advantages of the present invention will become better understood with reference to the following description and appended claims, and accompanying drawings where:

FIG. 17a-c show sample waveforms for the voltage, current, and instantaneous power of the discharge;

FIG. 20a-b show mean discharge power (a) and production rate of hydrogen peroxide (b) for various n-hexane to water feed ratios, the water flow rate being held constant at 0.5 mL/min while the organic flow rate was varied from 0 to 0.002, 0.005, 0.01, 0.02, and 0.04 mL/min.

Figure 1:
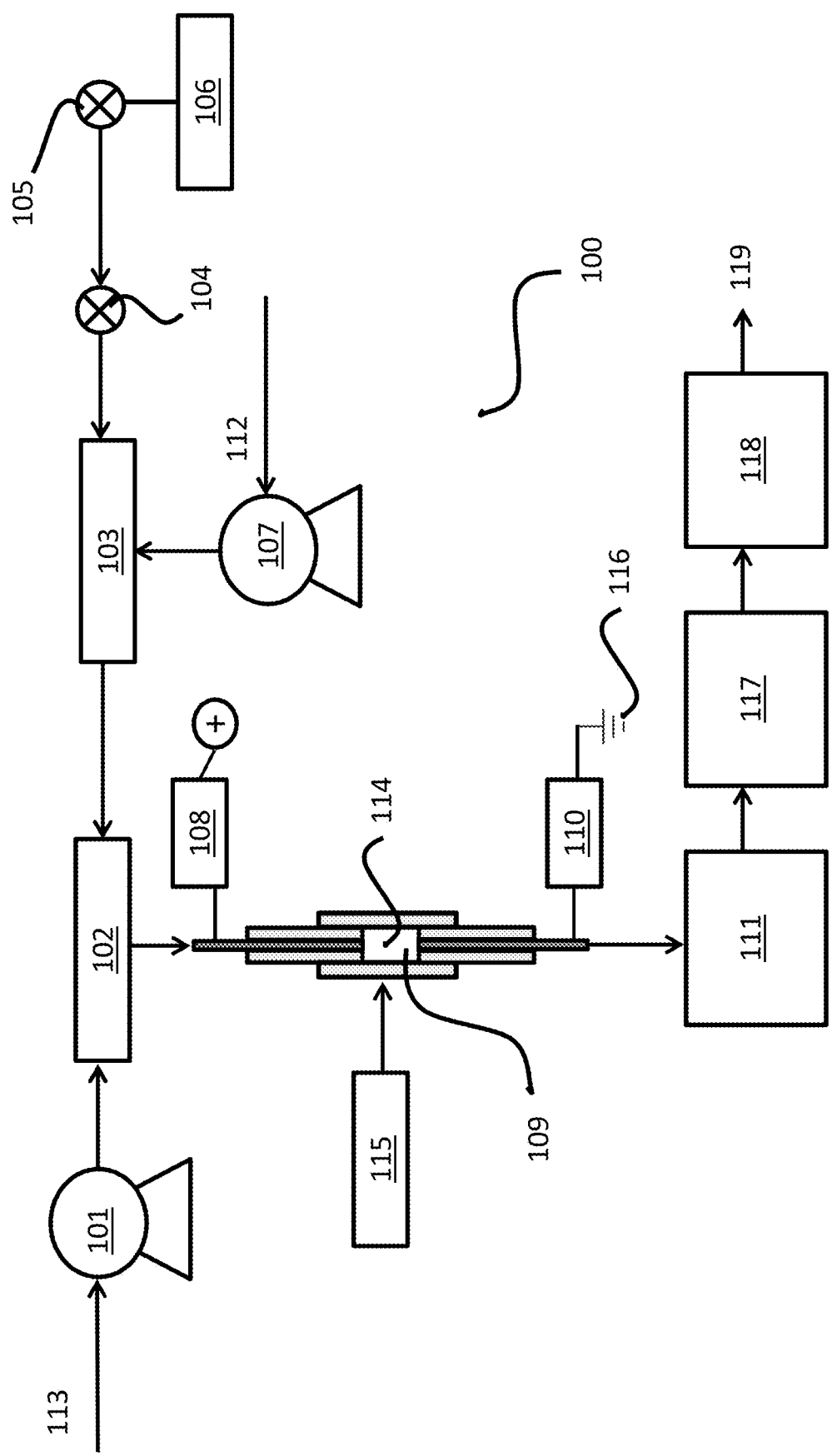
FIG. 1: is a schematic diagram of a process according to various embodiments.

It should be understood that the various embodiments are not limited to the arrangements and instrumentality shown in the drawings.

DETAILED DESCRIPTION OF THE INVENTION

The present invention utilizes a gas-water-organic plasma reactor for the conversion of alkanes into functionalized products (alcohols, aldehydes, etc.) using pulse plasma reactor with liquid water and flowing carrier gas. Hydrogen peroxide is also generated conjunction with the functionalized products.

The present invention may be understood more readily by reference to the following detailed description of preferred embodiments of the invention as well as to the examples included therein. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

As discussed above, there is a need to introduce selectivity, but depending on how this is accomplished it may come at the cost of lower conversion. Therefore, there is also a need to compensate for the lower conversion. According to various embodiments of the present invention, lower conversion can be compensated for in synthetic chemistry by reactor recirculation.

As discussed above, there is a need for greater predictability as to the location of the main chemical reactions. The physical location of the plasma chemical synthesis according to various embodiments of the present invention can depend, in part, on the volatility of the precursor molecule. Under conditions of low volatility (water), the plasma radicals may directly impinge on the droplet surface initiating reactions at the interface or even generate some radicals in the liquid phase. For high volatility cases (hexane), the plasma species will react in the gas phase.

As discussed above, there is a need to provide a modification of reactor/reaction conditions involving pulsing the power supply. Various embodiments of the present invention have shown (in the case of $H_2O_2$) that higher frequency pulses with lower energy per pulse can strongly increase energy yields.

According to various embodiments, an organic liquid (e.g., hexane which is immiscible with liquid water) is injected into a flowing gas (argon) stream followed by mixing with a liquid water stream. Thereafter, the mixture contacts a plasma region formed by a pulsed electric discharge. The plasma, which propagates along the interface between the flowing liquid and gas regions between the two electrodes, causes chemical reactions that generate various compounds. When hexane is used as the organic precursor NMR spectra clearly show the formation of 1-hexanol, 2-hexanol, and 3-hexanol. Indirect evidence strongly suggests the oxygenation is likely due to reaction of OH radicals formed from this dissociation of water by the plasma. Other spectra indicate the formation of the aldehyde (hexanal) and ketones (2-hexanone and 3-hexanone). It is also known that the plasma generates hydrogen peroxide ($H_2O_2$) by combination of said OH radicals. This work demonstrates the activation of the C—H bond using low temperature plasma with an inlet liquid stream such that value added products are formed effectively. This procedure combines two common chemical feed-stocks (hydrocarbon and water) and transforms them into the higher value functionalized organic products via a sequence of reactions where all necessary intermediate reactants are formed in situ using the electric discharge.

FIG. 1 shows a schematic diagram of a process 100 according to various embodiments. An organic liquid 112, such as n-hexane, can be pumped at a constant rate via a syringe pump 107, into a first mixing zone 103. The syringe pump 107 can have a 10 mL glass syringe. The first mixing zone 103 can be a nylon Swagelok tee joint. High pressure argon can be added to the first mixing zone 103 from a high pressure argon storage container 106 via a pressure regulator 105 where the flow rate is measured by a rotameter 104. Subsequently the organic liquid and the high pressure argon in the first mixing zone 103 can pass into a second mixing zone 102. The second mixing zone 102 can be a nylon Swagelok tee joint. DI water 113 can be pumped via a high-pressure pulse injection pump 101 into a second mixing zone 102. All of the contents of the second mixing zone, the organic liquid, the argon, and the DI water can be added to a reactor 109. The reactor 109 includes a plasma discharge region 114. Emission spectroscopy and/or high speed imaging 115 can be performed on the reactor 109. A high voltage (HV) probe 108 can be used to measure the voltage applied to the reactor. At the outlet of the reactor a shunt 110 can be used to measure the electrical current and thereby in combination with the voltage determine the power delivered to the reactor. A liquid effluent trap 111 can be used to collect the liquid exiting the reactor for subsequent chemical analysis. A power source 116 can supply a voltage at least one electrically-conductive inlet capillary and at least one electrically-conductive outlet capillary of the reactor 109, which are illustrated in greater detail in FIG. 2. Primary 117 and secondary 118 cold traps consisting of dry ice and acetone can also be employed to condense vaporized products not collected in the liquid effluent trap prior to the gas effluent exit 119.

Figure 2:
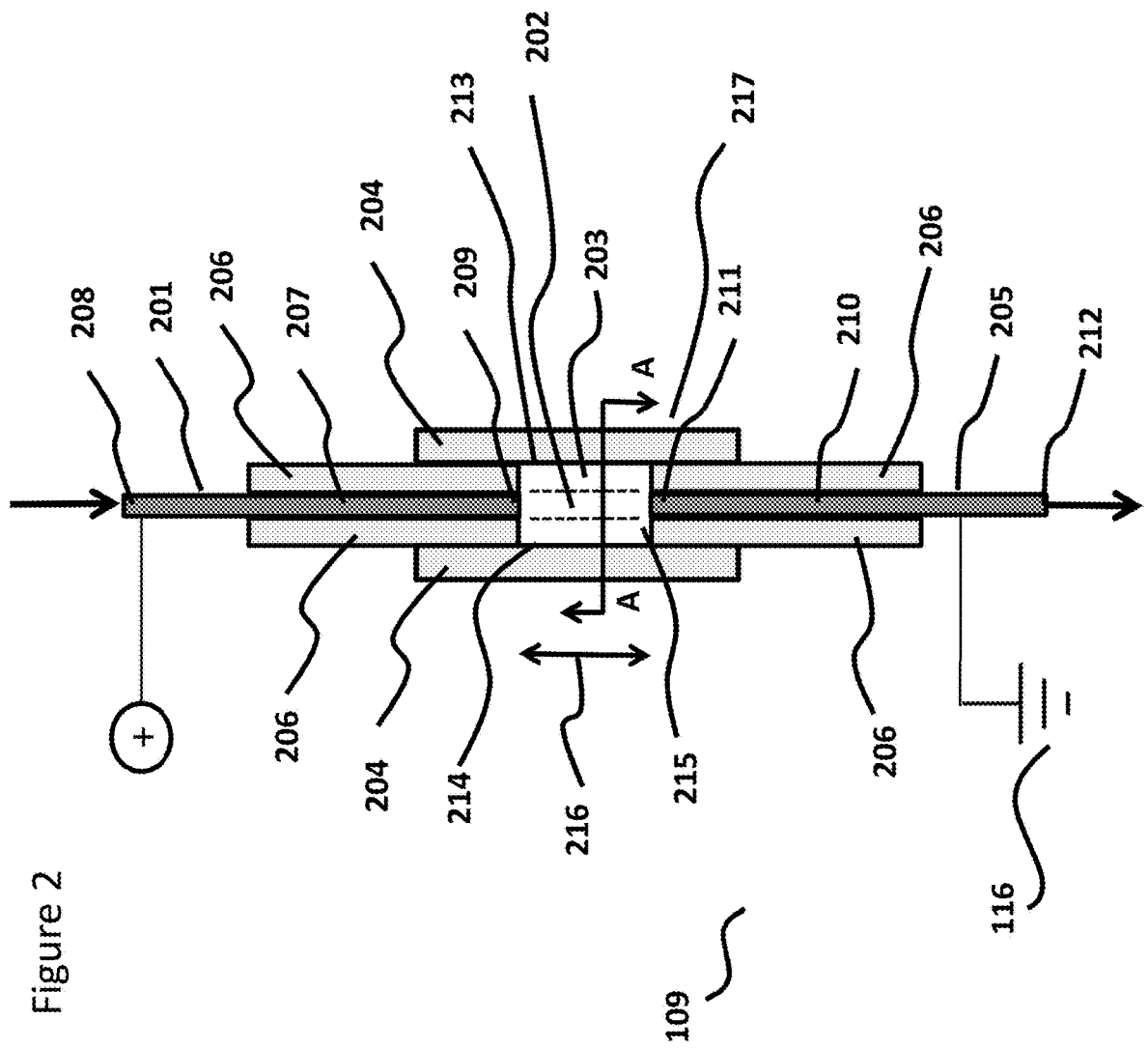
FIG. 2: shows an illustration of a vertical cross section of the plasma reactor according to various embodiments.

FIG. 2 shows an illustration of a vertical cross section of the plasma reactor 109 according to various embodiments. FIG. 2 shows a vertical cross section diagram of the reactor 109. Because of its simple construction from pre-fabricated materials, an added benefit to this reactor design is that it can be considered "disposable."

The reactor 109 can include a body portion 217 having one or more internal walls 213, 214 that define an internal cavity 215. According to various embodiments, and as shown in FIG. 2, the body portion 217 can be cylindrical.

The reactor 109 can include at least one electrically-conductive inlet capillary 201 having an inlet capillary body 207 extending between a fluid-receiving tip 208 and a fluid-injecting tip 209. The fluid-receiving tip 208 is positioned outside the internal cavity 215, and the fluid-injecting tip 209 is positioned inside the internal cavity 215.

The reactor can include at least one electrically-conductive outlet capillary 205 having an outlet capillary body 210 extending between a fluid-collecting tip 211 and a fluid-ejecting tip 212. The fluid-collecting tip 211 is positioned inside the internal cavity 215, and the fluid-ejecting tip 212 is positioned outside the internal cavity 215. The electrically-conductive inlet capillary 201 and the electrically-conductive outlet capillary 205 can be made of any electrically conductive material, for example, according to one particularly preferred embodiment the electrically-conductive inlet capillary 201 and the electrically-conductive outlet capillary 205 can be made a 316 stainless steel capillary tubing with an outer diameter (O.D.) of 1.59 mm (Restek). Other electrically-conductive materials, as described herein can also be employed. The capillaries can also be any shape, but are preferably cylindrical.

The fluid injecting tip 209 can be disposed relative to the fluid collecting tip 211 to generate a flowing liquid film region 203 on the one or more internal walls 213, 214 and a gas stream or a gas flow region 202 flowing through the flowing liquid film region 203, when a fluid is injected into the internal cavity 215 via the at least one electrically conductive inlet capillary 201. The fluid injecting tip 209 can be disposed relative to the fluid collecting tip 211 to propagate a plasma discharge along the flowing liquid film region 203 between the at least one electrically-conductive inlet capillary 201 and the at least one electrically-conductive outlet capillary 205. According to various embodiments, the fluid injecting tip 209 can be aligned with the fluid collecting tip 211.

According to particularly preferred embodiments, the internal walls 213, 214 can be the inner walls of a piece of fused quartz tubing 204 with an I.D. of 3.0 mm (AdValue Technology) which can serve as a viewing port for emission spectroscopy and high speed imaging. According to other particularly preferred embodiments, the electrically-conductive inlet capillary 201 and the electrically-conductive outlet capillary 205 can be incased by fused quartz tubing spacers 206 with an I.D. of 1.6 mm (AdValue Technology); the tubing 206 can be positioned such that the ends of the stainless steel and quartz tube spacers are flush at the entrance and exit of the discharge region, i.e. the internal cavity 215. These inlet and outlet assemblies comprising the electrically-conductive inlet capillary 201 and the electrically-conductive outlet capillary 205 incased by fused quartz tubing spacers 206 can then inserted into either end of the tubing 204.

The fluid injecting tip 209 and the fluid collecting tip 211 (or when employed, the respective ends of the inlet and outlet assemblies) can be positioned such that a gap 216 having a length. The gap 216 can have a length within a range having a lower limit and/or an upper limit. The range can include or exclude the lower limit and/or the upper limit. The lower limit and/or upper limit can be selected from 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 20.1, 20.2, 20.3, 20.4, 20.5, 20.6, 20.7, 20.8, 20.9, 21, 21.1, 21.2, 21.3, 21.4, 21.5, 21.6, 21.7, 21.8, 21.9, 22, 22.1, 22.2, 22.3, 22.4, 22.5, 22.6, 22.7, 22.8, 22.9, 23, 23.1, 23.2, 23.3, 23.4, 23.5, 23.6, 23.7, 23.8, 23.9, 24, 24.1, 24.2, 24.3, 24.4, 24.5, 24.6, 24.7, 24.8, 24.9, and 25 mm. For example, according to certain preferred embodiments, the gap 216 can have a length of about 4 mm.

The reactor can also include a power source 116, supplying a voltage across the at least one electrically-conductive inlet capillary and the at least one electrically-conductive outlet capillary. The power source 116 can be adapted to provide a pulsed current, a D.C. current, and/or an A.C. current between the at least one electrically-conductive inlet capillary 201 and the at least one electrically-conductive outlet capillary 205.

A ratio of the voltage to the length of the gap 216 can be within a range having a lower limit and/or an upper limit. The range can include or exclude the lower limit and/or the upper limit. The lower limit and/or upper limit can be selected from $2.5 \times 10^5$ V/m, $3 \times 10^5$, $4 \times 10^5$, $5 \times 10^5$, $6 \times 10^5$, $7 \times 10^5$, $8 \times 10^5$, and $9 \times 10^5$ V/m. For example, the body portion 217 can have a length, and a ratio of the voltage to the length can be at least about $2.5 \times 10^5$ V/m.

According to various embodiments, the body portion 217 can be cylindrical. The cylindrical body portion 217 can have a first diameter within a range having a lower limit and/or an upper limit. The range can include or exclude the lower limit and/or the upper limit. The lower limit and/or upper limit can be selected from 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.01, 1.02, 1.03, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, 1.99, and 2 cm. For example, according to certain preferred embodiments, the cylindrical body portion 217 can have a first diameter 0.1 to 1 cm. The at least one electrically-conductive inlet capillary can have a second diameter that is less than the first diameter. The at least one electrically-conductive outlet capillary can have a third diameter that is greater than the second diameter and less than the first diameter.

Figure 3A:
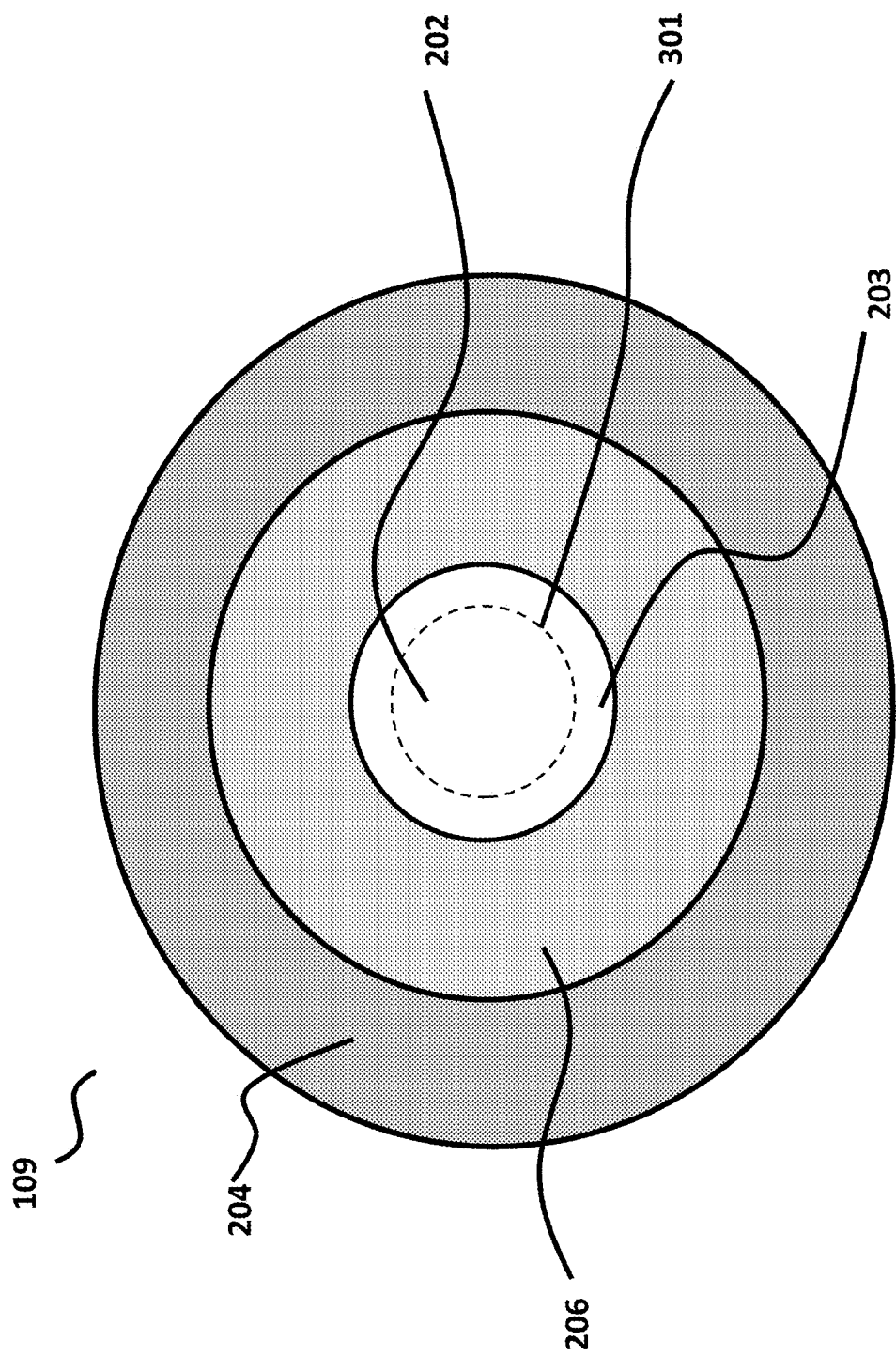
FIG. 3a-d: show illustrations cross sections of various embodiments of the plasma reactor.

FIG. 3a shows an illustration of a radial cross section along line A-A as shown in FIG. 2 of the plasma reactor 109 according to various embodiments. A horizontal cross section of the discharge region is shown in FIG. 3. The gas flow region 202 can be bounded by a gas/liquid interface 301, separating the gas flow and plasma discharge region 202 from the liquid film flow region 203. The gas/liquid interface 301 can be, but need not always be highly turbulent. As discussed under FIG. 2, the liquid film flow region 203 flows along the fused quartz tubing 204 which acts as the reactor wall.

According to various embodiments, the gas flow can be determined by the nozzle, i.e. the outlet of a capillary, diameter and the pressure. The liquid flow can be determined by the gas flow, and all other dependent properties can thereafter be determined. The maximum liquid flow can be determined by the gas flow, and all other dependent properties can thereafter be determined. The pressure of the inlet gas can be in the range of 10 to 500 pounds per square inch (psi). For an inlet gas pressure of 60 psi and a 0.01 inch inlet capillary nozzle with a 3 mm tube, the gas flow is 0.3 liters per minute and the upper liquid flow can be 4 ml/min. In addition to scaling up this process up by placing many single reactors in parallel, alternative geometries could be used which utilize a single large volume chamber for the flow of water and gas in conjunction with multiple inlet and outlet nozzles into and out of the single chamber.

Figure 3B:
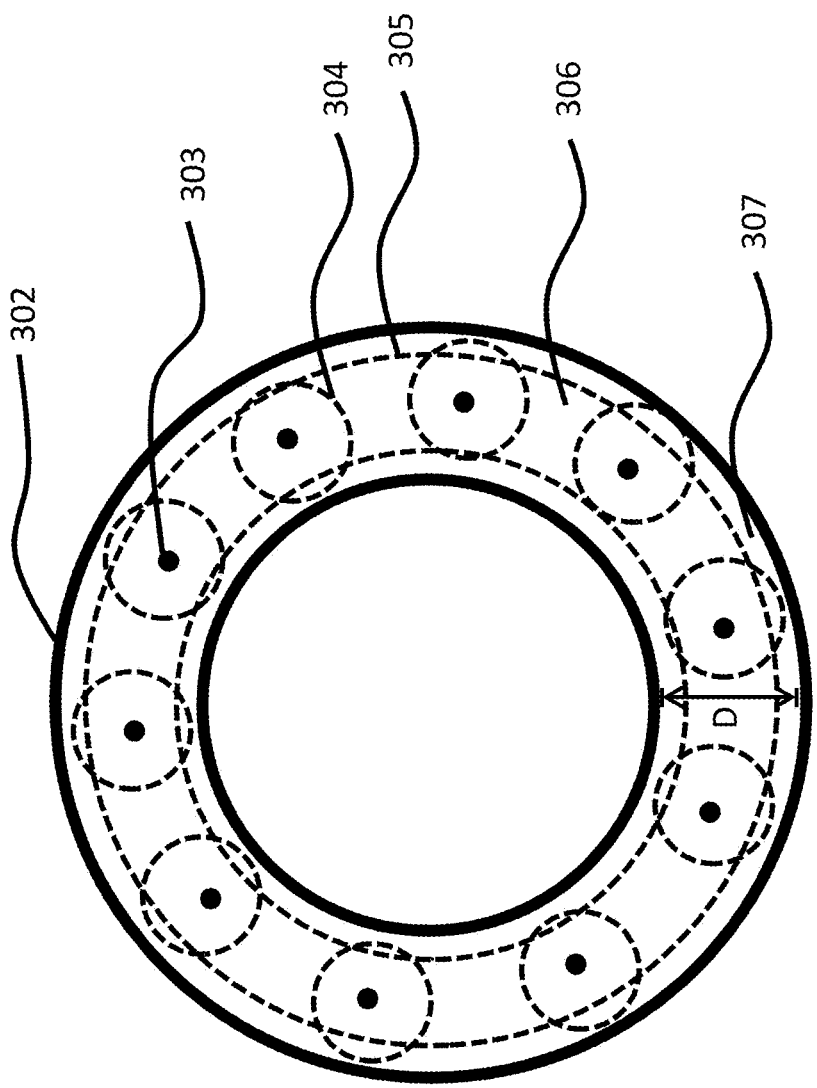

FIG. 3b shows an illustration of a radial cross section of an exemplary configuration comprising a reactor body 302 and a plurality of electrically-conductive inlet capillaries 303. The reactor body 302 is an annular ring and has a distance D between its walls. Each of the electrically-conductive inlet capillaries 303 can have a range of influence 304 within the reactor body 302. Inside its range of influence each electrically-conductive inlet capillary can be used to form a plasma discharge. One or more electrically-conductive outlet capillaries (not shown) can be aligned with or otherwise positioned relative to the plurality of electrically-conductive inlet capillaries 303 to generate a flowing liquid film region on one or more internal walls of the reactor body 302 and a gas stream or a gas flow region flowing through the flowing liquid film region, when a fluid is injected into the internal cavity via the at least one electrically conductive inlet capillary 303. The one or more electrically-conductive outlet capillaries (not shown) can additionally or alternatively be aligned with or otherwise positioned relative to the plurality of electrically-conductive inlet capillaries 303 to propagate a plasma discharge along the flowing liquid film region between one or more of the plurality of electrically-conductive inlet capillaries 303 and one or more of the one or more plurality of electrically-conductive outlet capillaries. As shown, a gas liquid interface 305 can be generated between a liquid film region 307 and a gas flow region 306 passing across the liquid film region 307.

Figure 3C:
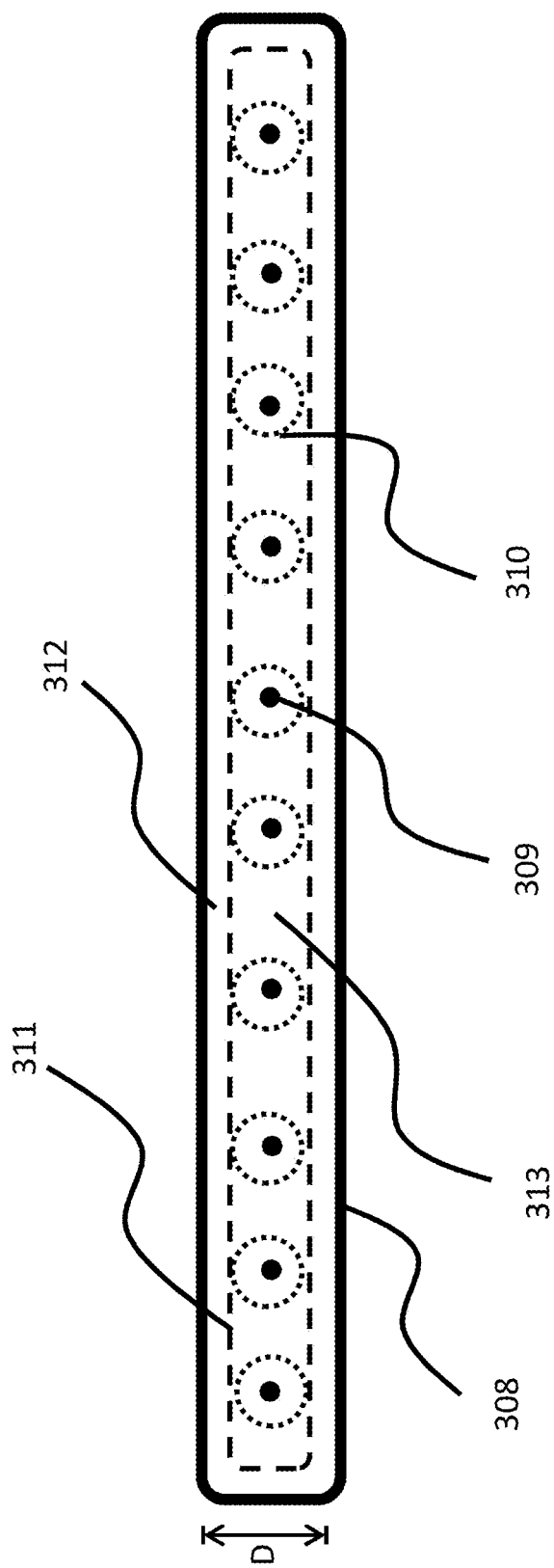

FIG. 3c shows an illustration of a radial cross section of an exemplary configuration comprising a reactor body 308 and a plurality of electrically-conductive inlet capillaries 309. The reactor body 308 is an elongated box and has a distance D between its walls. Each of the electrically-conductive inlet capillaries 309 can have a range of influence 310 within the reactor body 308. Inside its range of influence each electrically-conductive inlet capillary can be used to form a plasma discharge. One or more electrically-conductive outlet capillaries (not shown) can be aligned with or otherwise positioned relative to the plurality of electrically-conductive inlet capillaries 309 to generate a flowing liquid film region on one or more internal walls of the reactor body 308 and a gas stream or a gas flow region flowing through the flowing liquid film region, when a fluid is injected into the internal cavity via the at least one electrically conductive inlet capillary 309. The one or more electrically-conductive outlet capillaries (not shown) can additionally or alternatively be aligned with or otherwise positioned relative to the plurality of electrically-conductive inlet capillaries 309 to propagate a plasma discharge along the flowing liquid film region between one or more of the plurality of electrically-conductive inlet capillaries 309 and one or more of the one or more plurality of electrically-conductive outlet capillaries. As shown, a gas liquid interface 311 can be generated between a liquid film region 312 and a gas flow region 313 passing through the liquid film region 312.

Any configuration of the reactor body can be employed. The configurations shown in FIG. 2, FIG. 3a, FIG. 3b, and FIG. 3c are merely exemplary. Any geometry can be employed.

Figure 3D:
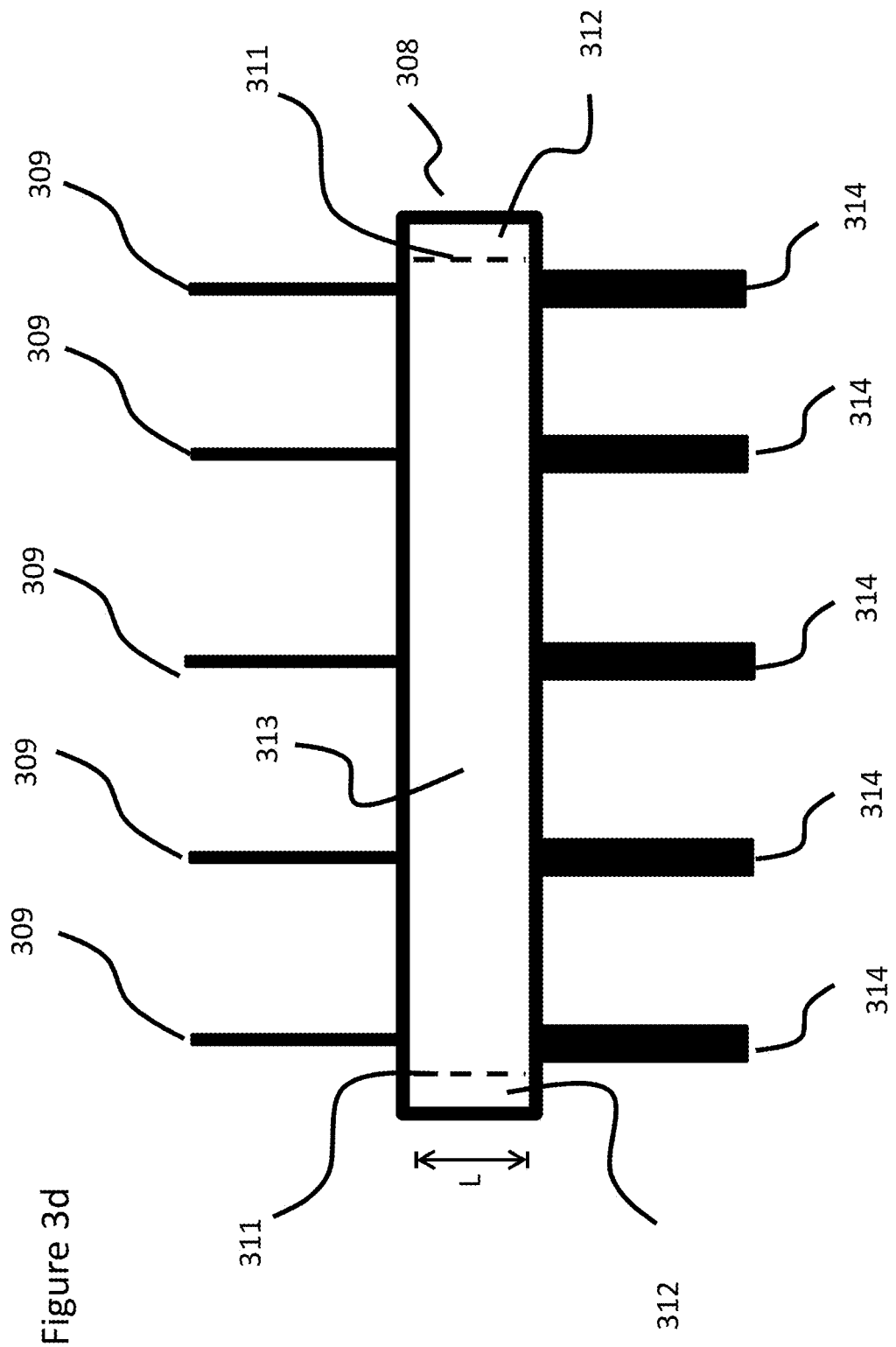

FIG. 3d shows a vertical cross-section of a reactor body 308 as depicted in either FIG. 3b or 3c. Since the vertical cross section would be the same for both the reactor body could have been designated with reference numeral 302. Reference numerals in the specific embodiment shown in FIG. 3d correspond to those in FIG. 3c. Again, since the vertical cross section would be the same for FIG. 3b, the reference numerals of FIG. 3b could have been used. FIG. 3d also shows a plurality of electrically-conductive outlet capillaries 314. The electrically-conductive outlet capillaries 314 are shown in alignment with the electrically-conductive inlet capillaries 309. FIG. 3c also illustrates a length L of the reactor body 308.

Various embodiments relate to a method comprising injecting a mixture comprising liquid water, a gas, and an organic compound, into at least one electrically-conductive inlet capillary tube of a continuously-flowing plasma reactor to generate a flowing liquid film region on one or more internal walls of the continuously-flowing plasma reactor with a gas stream flowing through the flowing liquid film region; propagating a plasma discharge along the flowing liquid film region from at least one electrically-conductive inlet capillary to an electrically-conductive outlet capillary tube at an opposing end of the continuously-flowing plasma reactor; dissociating the liquid water in the plasma discharge to form a plurality of dissociation products; producing hydrogen peroxide from the plurality of dissociation products; dissolving the hydrogen peroxide into the flowing liquid film region; and recovering at least a portion of the hydrogen peroxide from the electrically conductive outlet capillary.

The mixture can be injected into a plurality of electrically-conductive inlet capillary tubes. The flowing liquid film region can have an annular shape. The gas stream can flow through the center of the flowing liquid film region. For example, the gas stream can flow through a central portion of the annularly shaped flowing liquid film region.

The plasma discharge can have a nominal frequency within a range having a lower limit and/or an upper limit. The range can include or exclude the lower limit and/or the upper limit. The lower limit and/or upper limit can be selected from 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, and 600 Hz. For example, according to certain preferred embodiments, the plasma discharge can have a nominal frequency of 500 Hz.

The plasma discharge can have a frequency within a range having a lower limit and/or an upper limit. The range can include or exclude the lower limit and/or the upper limit. The lower limit and/or upper limit can be selected from 50, 60, 70, 80, 90, 100, 110, 120, 130, 140, 150, 160, 170, 180, 190, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, and 12000 Hz. For example, according to certain preferred embodiments, the plasma discharge can have a frequency of from about 100 to 10000 Hz.

According to various embodiments, the method can further include generating at least one functionalized product from the organic liquid and the plurality of dissociation products in the plasma discharge. The functionalized product can be, but is not limited to an alcohol, a ketone, an aldehyde, an ester, an organic acid, an organic peroxide, and combinations thereof. For example, the functionalized product can an alcohol, including but not limited to methanol, hexanol, decanol, cyclohexanol, phenol, phenethyl alcohol, benzyl alcohol, and combinations thereof. For example, the functionalized product can be a ketone, including but not limited to butanone, hexanone, cyclopentanone, cyclohexanone, propiophenone, benzophenone, and combinations thereof. For example, the functionalized product can be an aldehyde, including but not limited formaldehyde, hexanal, cyclopentanal, cyclohexanal, benzaldehyde, tolualdehyde, and combinations thereof. For example, the functionalized product can be an ester, including but not limited to ethyl acetate, ethyl formate, ethyl isovalerate, isobutyl acetate, propyl isobutyrate, ethyl acetate, benzyl acetate, methyl phenylacetate, and combinations thereof. For example, the functionalized product can be an organic acid, including but not limited to acetic acid, butyric acid, hexanoic acid, cyclohexanecarboxylic acid, benzoic acid, and combinations thereof. For example, the functionalized product can be an organic peroxide, including but not limited to peracetic acid, hydroperoxyhexane, methyl hydroperoxide, cyclohexane peroxide, benzoyl peroxide, and combinations thereof.

According to other embodiments, the method can further include recovering the generated hydrogen peroxide and the functionalized organic products. According to various embodiments, the hydrogen peroxide dissolved into the flowing liquid film region can be protected from degradation as the hydrogen peroxide flows through the flowing liquid film region and exits the continuously-flowing plasma reactor via the electrically conductive outlet capillary.

The liquid water can have a temperature within a range having a lower limit and/or an upper limit. The range can include or exclude the lower limit and/or the upper limit. The lower limit and/or upper limit can be selected from 0, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, 56, 56.5, 57, 57.5, 58, 58.5, 59, 59.5, 60, 60.5, 61, 61.5, 62, 62.5, 63, 63.5, 64, 64.5, 65, 65.5, 66, 66.5, 67, 67.5, 68, 68.5, 69, 69.5, 70, 70.5, 71, 71.5, 72, 72.5, 73, 73.5, 74, 74.5, 75, 75.5, 76, 76.5, 77, 77.5, 78, 78.5, 79, 79.5, 80, 80.5, 81, 81.5, 82, 82.5, 83, 83.5, 84, 84.5, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5, 99, 99.5, 100, 100.5, 101, 101.5, 102, 102.5, 103, 103.5, 104, 104.5, 105, 105.5, 106, 106.5, 107, 107.5, 108, 108.5, 109, 109.5, 110, 110.5, 111, 111.5, 112, 112.5, 113, 113.5, 114, 114.5, 115, 115.5, 116, 116.5, 117, 117.5, 118, 118.5, 119, 119.5, and 120 degrees Celsius. For example, according to certain preferred embodiments, the liquid water can have a temperature of from greater than 0 to less than 100 degrees Celsius.

The reactor can have a pressure within a range having a lower limit and/or an upper limit. The range can include or exclude the lower limit and/or the upper limit. The lower limit and/or upper limit can be selected from 0.01, 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, and 4 bar. For example, according to certain preferred embodiments, the reactor can have a pressure of from approximately 0.1 to 2 bar.

The liquid water has a conductivity within a range having a lower limit and/or an upper limit. The range can include or exclude the lower limit and/or the upper limit. The lower limit and/or upper limit can be selected from 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, and 700 microSiemens/cm. For example, according to certain preferred embodiments, the liquid water has a conductivity 1 to 500 microSiemens/cm.

The gas can be a diatomic gas, a noble gas, and combinations thereof. The diatomic gas can be hydrogen, nitrogen, fluorine, oxygen, iodine, chlorine, bromine, and combinations thereof. The noble gas can be helium, neon, argon, krypton, xenon, radon, and combinations thereof.

The organic liquid can be an alkane, an alkene, an aromatic hydrocarbon, and combinations thereof. The alkane can have a structure selected from linear, cyclic, branched, and combinations thereof. The alkane can be a C1-C20 alkane. The alkane can be, but is not limited to, methane, ethane, propane, butane, hexane, octane, decane, Icosane and combinations thereof. The alkene can have a structure selected from linear, cyclic, branched, and combinations thereof. The alkene can be a C2-C20 alkene. The alkene can be, but is not limited to ethylene, propylene, hexenes, octenes, decenes, pentadecenes and combinations thereof. The aromatic hydrocarbon can include from 6 to 20 carbon atoms. The aromatic hydrocarbon can be, but is not limited to, benzene, toluene, ethylbenzene, xylenes, cumene, biphenyl, anthracene, and combinations thereof.

The at least one electrically-conductive inlet capillary and the at least one electrically-conductive outlet capillary can include an electrically conductive material. The electrically conductive material can be, but is not limited to stainless steel, nickel alloys, chromium alloys, titanium alloys, molybdenum alloys, copper alloys, gold alloys, platinum alloys, zinc alloys, zirconium alloys, and combinations thereof.

Figure 4B:
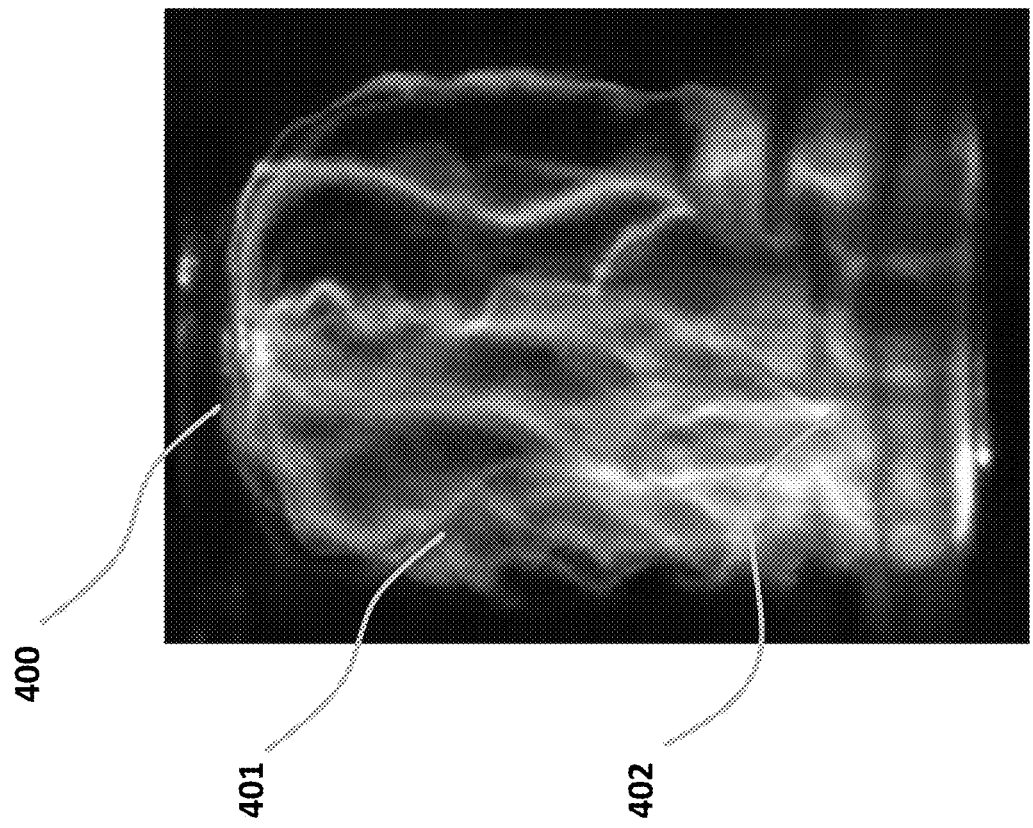
FIG. 4a-c: are photographs of the plasma discharge with a) rapid shutter speed ($\frac{1}{12000}$ sec) b) a long exposure time ($\frac{1}{60}$ sec), c) a view showing the liquid/gas interface.
Figure 4A:
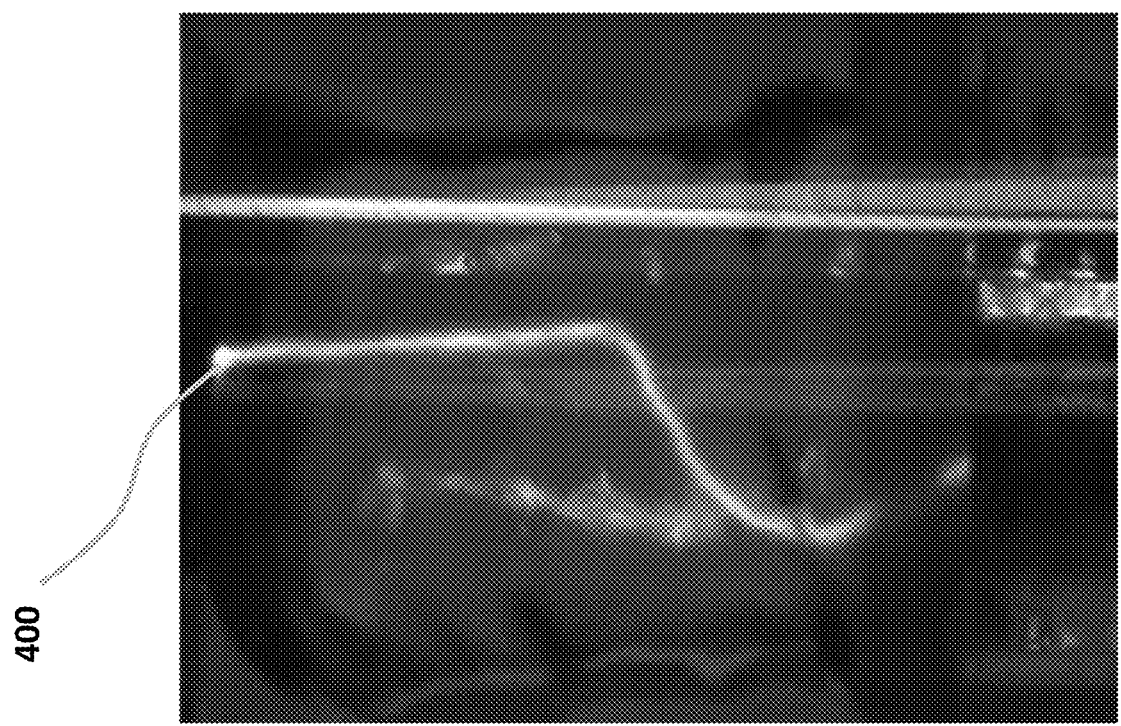
Figure 4C:
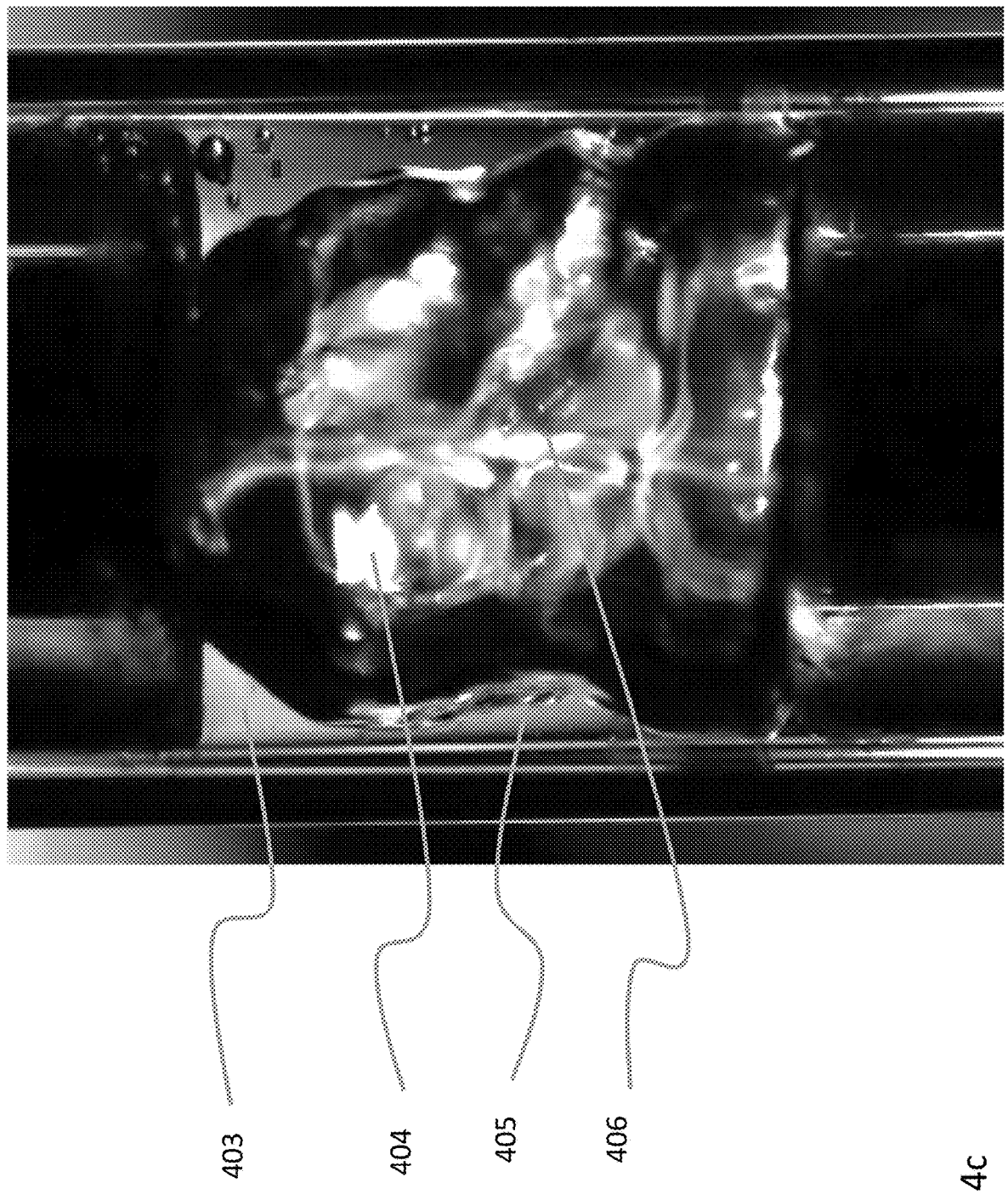

FIGS. 4a, 4b, and 4c depict high speed imaging of the plasma discharge region. FIG. 4a shows a single plasma channel 400 propagating between electrodes and along the gas liquid interface. FIG. 4b, with a long photographic exposure, shows multiple plasma channels 400, 401, and 402 propagating between electrodes. FIG. 4c shows a liquid film region 403, and a gas flow region 404, separated by a liquid/gas interface 405. A plasma discharge 406 is also shown at the liquid/gas interface 405.

The invention is further described in the following illustrative examples in which all parts and percentages are on a molar basis unless otherwise indicated.

Examples

According to the present disclosure, vaporized n-hexane in a flowing argon carrier gas was mixed with deionized liquid water and injected into a tubular plasma reactor. A liquid water film forms on the wall of the tubular reactor and plasma channels propagate along the gas-liquid interface. Gas-chromatography mass spectrometry (GC-MS) and nuclear magnetic resonance (NMR) spectroscopic analysis of the major products and their relative ratios collected in the effluent of the reactor confirm the formation of 3-hexanol (26%), 2-hexanol (21%), 3-hexanone (17%), 2-hexanone (17%), 1-hexanol (11%), and hexanal (8%). The functionalization is likely due to oxidation of the organic stating material by OH radicals formed from the dissociation of water by the plasma. The functionalization of cyclohexane was achieved in the same manner where analysis showed the formation of cyclohexanone (47%), cyclohexene (20%), cyclohexanol (19%), hexanal (11%), and 2-cyclohexenone (2%). Hydrogen peroxide was also produced in the presence of either organic compound and the amount formed decreased as the amount of organic flowing into the reactor was increased. It is likely that the hydrogen peroxide is formed in the gas phase close to the gas-liquid interface by OH radical recombination. This work demonstrates the activation of the C—H bond using low temperature plasma by combining two common chemical feed-stocks (hydrocarbon and water) and transforming them into the higher value functionalized organic products via a sequence of reactions where all necessary intermediate reactants are formed in situ by the electric discharge.

Reactor and Apparatus

The Examples employ a process as illustrated in FIG. 1, which shows the general process schematic of the experimental setup. High purity argon gas (Air Gas; Tallahassee, Fla.) at 414 kPa was utilized, resulting in a flow rate of 0.5 L/min as measured by a rotameter (Cole Palmer; Vernon Hills, Ill.). The argon was allowed to flow unrestricted into the reactor inlet. The argon flow rate is a function of the pressure head and the inner diameter (I.D.) of the reactor inlet nozzle (0.25 mm). The argon gas contacts a small amount of liquid organic such as n-hexane or cyclohexane at Mixing Zone 1 which was a $\frac{1}{16}$" Swagelok® nylon tee joint, Jax Fluid System Technologies; Jacksonville, Fla. The liquid organic was pumped at a constant rate of 0.002 mL/min with a syringe pump (Harvard Apparatus, PhD 2000 Infusion; Holliston, Mass.) equipped with a 10 mL glass syringe (Hamilton, GASTIGHT; Reno, Nev.).

Due to the small amount of n-hexane or cyclohexane used in comparison to the argon flow rate and their high volatility, the organic liquid rapidly vaporized into the gas phase. The process can be easily adapted to utilize organic liquids other than n-hexane or cyclohexane. The resulting gas phase mixture then contacts a liquid stream of deionized water flowing at 0.5 mL/min (pH—5.0±0.2, conductivity—5.0±1.0 µS/cm) at Mixing Zone 2 ($\frac{1}{16}$" Swagelok® nylon tee joint, Jax Fluid System Technologies; Jacksonville, Fla.). The deionized water was delivered to the system with a high pressure, pulse injection pump (Optos Series, Eldex Laboratories Inc.; Napa, Calif.).

High pressure mixing occurs between these three components (argon, organic, and water) in Mixing Zone 2, after which the mixture flows through the inlet nozzle of the reactor and into the plasma discharge region where chemical reactions are induced.

After exiting the discharge region, the liquid phase of the effluent was directly collected in a vessel while the gas phase was allowed to flow through a series of condensers submerged in cold baths consisting of dry ice and acetone (−78° C.) in order to condense out any compounds still vaporized in the argon gas. A four hour run time was utilized where afterwards the resulting three liquid phases were analyzed individually using GC-MS, NMR and UVis spectroscopy.

The reactor was constructed from pre-fabricated round tubing giving it a cylindrical geometry. FIG. 2 shows a vertical cross section diagram of the reactor. Because of its simple construction from pre-fabricated materials, an added benefit to this reactor design is that it can be considered "disposable." The inlet and outlet parts of the reactor are made of 316 stainless steel capillary tubing with an outer diameter (O.D.) of 1.59 mm (Supelco; Bellefonte, Pa.) and are incased by fused quartz tubing spacers with an inner diameter (I.D.) of 1.6 mm (AdValue Technology; Tucson, Ariz.); the tubing was positioned such that the ends of the stainless steel and quartz tube spacers were flush at the entrance and exit of the discharge region. The inlet and outlet assemblies were then inserted into either end of an additional piece of fused quartz tubing with an I.D. of 3.0 mm (AdValue Technology; Tucson, Ariz.) which served as the reactor wall and viewing port for emission spectroscopy and high speed imaging. The inlet and outlet assemblies were positioned such that a 4 mm gap existed between the entrance and exit of the discharge region. A horizontal cross section of the discharge region is shown in FIG. 3a.

A key aspect of this reactor system is the flow pattern generated inside the reactor volume. Because the inlet capillary tube has an internal diameter (I.D.) of 0.25 mm and that of the discharge region is 3 mm, a well-mixed radial spray is generated as the high pressure mixture exits the inlet nozzle and enters the reactor volume. Due to the constriction at the reactor inlet, high pressure mixing occurs between the components which exit from Mixing Zone 2 in FIG. 1. Because the inlet capillary tube has an inner diameter of 0.25 mm and that of the discharge region is 3 mm, a well-mixed radial spray is generated as the high pressure mixture exits the inlet capillary and enters the reactor volume. This spray then rapidly contacts the reactor wall creating a liquid film which flows along the reactor wall coupled with a high velocity gas flow region in the radial center of the reactor.

High speed imaging was performed with a VW-9000 series high speed microscope system with a VH-00R 0-50× lens (Keyence; Itasca, Ill.) to confirm the existence and analyze the previously mentioned flow regions. FIG. 4a is a photograph of the reaction plasma zone region taken with a rapid shutter speed ($\frac{1}{12000}$ sec) and captures not only a single filamentous plasma channel, but also the wave-like pattern of water flow on the walls of the reactor. FIG. 4b depicts a long exposure time ($\frac{1}{60}$ sec) and captures the many filamentous plasma channels produced during this time period. Both photos (FIGS. 4a and 4b) indicate that the discharge takes place along the gas-liquid interface and not within the liquid film flow region or in the middle of the gas stream; the majority of the plasma streamers appear to travel along the gas liquid interface. In FIG. 4b the reddish streamer channels arise from the water flow while the lighter bluish-green parts come from the organic vapor.

An additional key aspect of this reactor design was that the stainless steel capillary tubing which acted as the entrance and exit to the reactor volume also function as the anode and cathode which generate the plasma discharge as shown in FIG. 1. This configuration provides maximum contact of the reactants with the plasma by minimizing by-pass regions where the gas-liquid flow does not contact the plasma. In the specific setup the high voltage lead was attached to the inlet nozzle of the reactor while the outlet capillary was grounded. The power supply and pulse forming circuit is similar to that used in our previous work. The power supply (DC 1740B BK Precision; Yorba Linda, Calif.) was driven by a pulse generator (2 MHz 4010A BK Precision; Yorba Linda, Calif.) to provide pulsed 12 V direct current to an automobile ignition coil (VW-AG, ERA Germany). A high voltage diode was placed between the ignition coil and the reactor to protect the coil from unwanted upstream voltage surges back to the ignition coil from the reactor. The pulse frequency and duty cycle was held constant for all experiments at 500 Hz and 40%.

Figure 5:
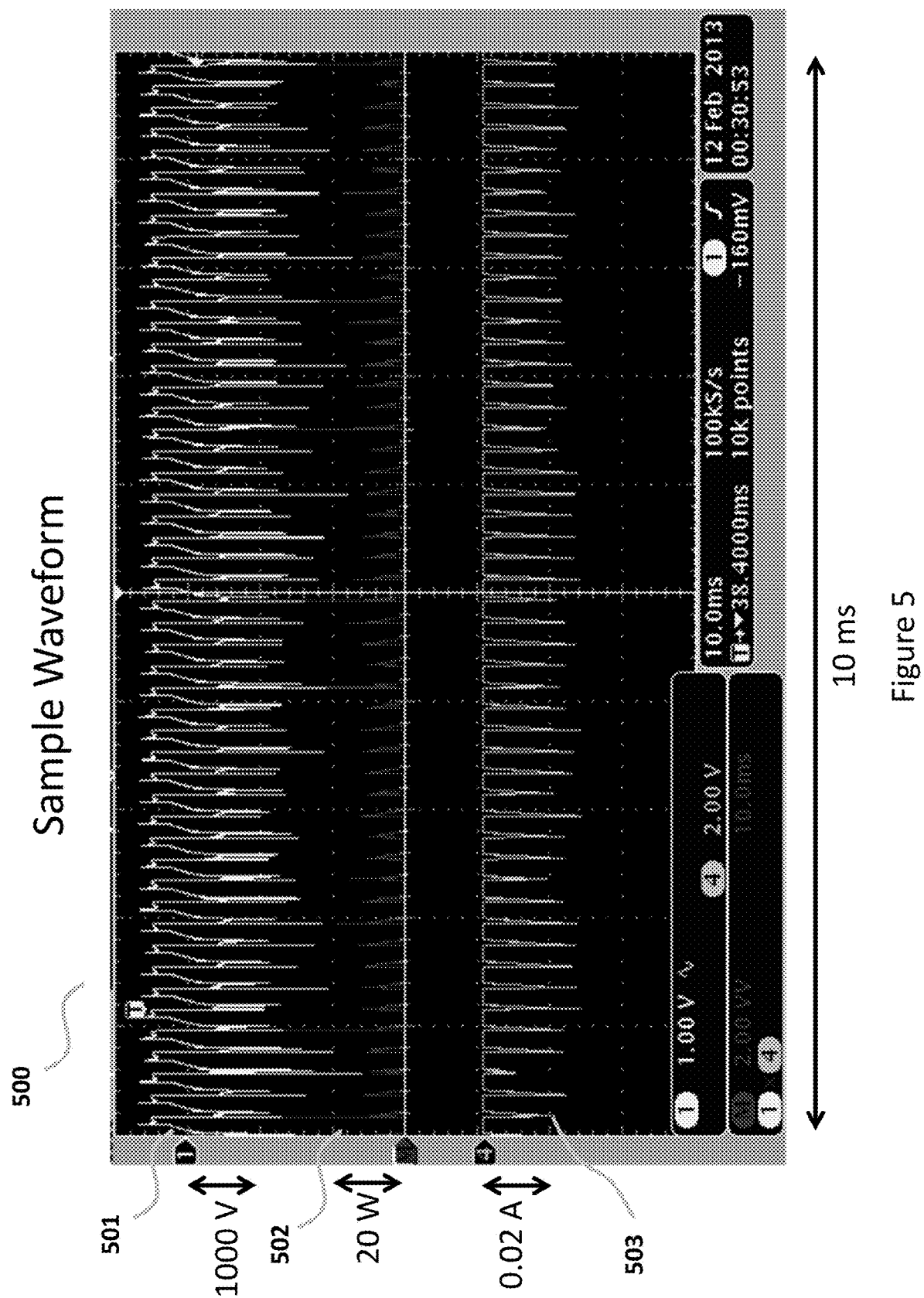
FIG. 5: is a sample waveform of discharge.

The voltage, current, and power waveforms of the discharge were measured with a Tektronix DPO 3014 oscilloscope (Tektronix Inc.; Beaverton, Oreg.). The sampling rate of the oscilloscope was $10^4$ points for the 100 ms acquisition window. The discharge voltage was measured with a high-voltage probe (P6015 Tektronix; Beaverton, Oreg.) connected to the lead electrode. The current was measured with a 100Ω shunt to the ground in the secondary of the ignition coil. The math function of the oscilloscope was used to generate the calculated power pulses. FIG. 5 is a screen shot of a measurement from said oscilloscope 500. Power 502 (watts) is shown in red, current 503 (amps) is shown in green, and voltage 501 (volts) is shown in yellow. Averages of three power measurements for each trial were taken to reduce the error of the measurement and exported to Excel where the magnitude of the individual data points were averaged to provide a mean power for the time period of the acquisition window. The instantaneous power was calculated by multiplication of the individual data points in the current and voltage waveforms. The mean discharge power was determined by averaging the instantaneous power across the time period of acquisition window. Sample current, voltage, and power waveforms are shown in FIGS. 17*a*-*c*. It should be noted that the power reported in this study was the "power delivered to the discharge" and that the overall efficiency also depends upon the power and efficiency of the transformer.

After exiting the reactor the liquid and gas effluent are separated and analyzed using NMR and Gas Chromatography.

NMR and Chemical Analysis

Figure 6:
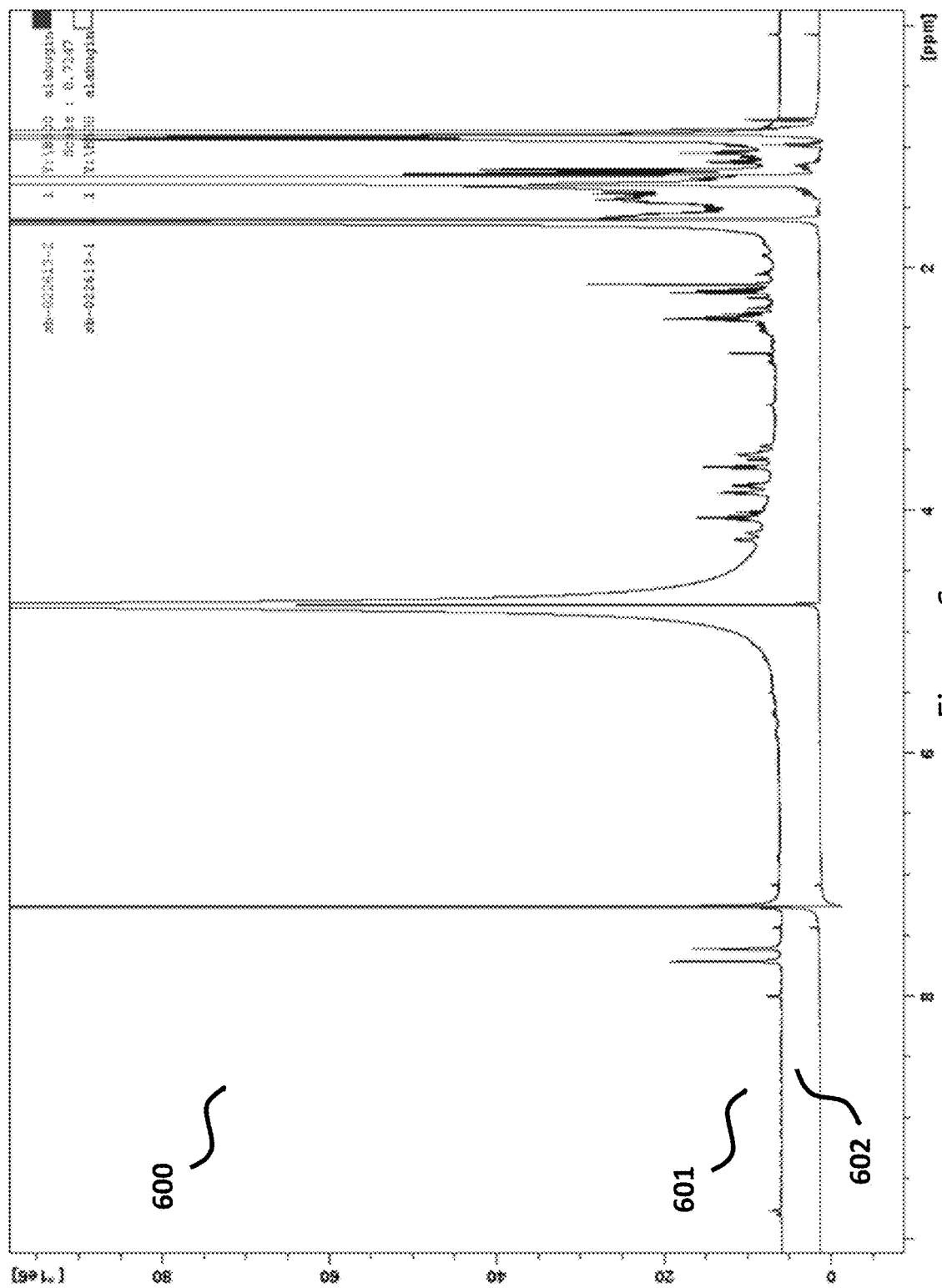
FIG. 6: is a complete NMR-spectra for sample run with 0.5 ml/min water, 0.002 ml/min hexane and 0.5 L/min Argon.

A vial containing 30 ml of sample from the reactor—consisting of only an aqueous layer—is extracted with 1 ml of deuterated chloroform, which is then retrieved and pipetted into an empty NMR test tube. The same procedure is repeated on a reference sample based on the same flow rates of hexane, water and argon but without activated plasma discharge. Subsequently, both spectra are compared in order to distinguish products from prevalent impurities in the starting materials (FIG. 6). FIG. 6 is a complete NMR-spectra 600 for sample run with 0.5 ml/min water, 0.002 ml/min hexane and 0.5 L/min Argon. Item 602 shown in red indicates the control sample not exposed to the electrical discharge. Item 601 shown in blue indicates a liquid sample collected downstream of the electrical discharge reactor in the liquid effluent trap shown in FIG. 1 as 111. The NMR acquisition time of 1 hour (1000 runs) provides sharp 1H proton NMR spectra. The NMR system was a Bruker 600 MHz Ultrashield. Reference spectra are obtained mostly from the "Spectral Database of Organic Compounds, SDBS" organized by the National Institute of Advanced Industrial Science and Technology (AIST), Japan (http://sdbs.riodb.aist.go.jp/sdbs/cgi-bin/cre_index.cgi?lang=eng), unless otherwise stated.

The concentration of hydrogen peroxide formed in the liquid fractions was measured using a colorimetric test with a UV-Vis spectrophotometer (Perkin-Elmer, Lambda 35; Waltham, Mass.) where 2 mL liquid samples were taken and mixed with 1 mL of a titanium oxysulfate-sulfuric acid complex. The absorbance of the formed yellow complex was measured at a 410 nm wavelength and converted to hydrogen peroxide concentration by a calibration curve generated with stock solutions of hydrogen peroxide where concentration was confirmed by titration with 0.1 N potassium permanganate.

For GC-MS analysis, the three separate aqueous fractions collected from the reactor were combined, extracted with chloroform, and dried over sodium sulfate. The resulting extract was then left open to the atmosphere for a period of time in order to concentrate the products by solvent evaporation. The analysis was performed on a Clarus 500 GC with an Elite-Wax column length of 30 m and diameter size of 250 μm in conjunction with a Clarus 550d MS (Perkin Elmer). Standards of the identified products as well as the starting materials were utilized to provide additional verification for the identified compounds.

For NMR analysis, successive extractions on the three separate aqueous fractions collected from the reactor were performed with deuterated chloroform and the resulting extracts dried over sodium sulfate. Analysis of each individual fraction was executed with a 600 MHz Ultrashield (Bruker) where an acquisition time of 1 hour was utilized. Identification of the product compounds was performed by comparing the chemical shift and the multiplicity of key NMR signature peaks of the particular compound to reference NMR spectra obtained from the "Spectral Database of Organic Compounds, SDBS" organized by the National Institute of Advanced Industrial Science and Technology, Japan. In most cases the signature peaks originated from functional groups bonded closely to the main characteristic functional group, i.e. $CH_3$ bonded to a carbonyl group. A quantitative analysis on the three liquid fractions collected was also performed with NMR by adding known concentrations of benzyl phenyl ether to the three separate extracts of the aqueous phases. The integrated signals of all functional groups of interest were then compared with the integrated singlet signal of the benzyl phenyl ether $CH_2$-group at 5.05 ppm to allow the back calculation of the concentration of each compound.

Results

FIGS. 7 to 12 show example NMR spectra demonstrating the presence of reaction products from hexane. The main products identified are 1-hexanol, 2-hexanol, 3-hexanol, hexanal, 2-hexanone, and 3-hexanone. Additional products showing other NMR peaks not illustrated here have not yet been identified. The identification of the product compounds was performed by comparing the NMR shift as well as the multiplicity of key signature peaks of the particular compound. Usually the signature peaks originate from functional groups bonded closely to the main functional group, i.e. $CH_3$ bonded to a carbonyl group or $CH_2$ directly bonded to the oxygen of an alcohol. Peaks from other parts of the molecule usually cannot be used for identification since they overlap with very similar groups from other products.

Figure 7:
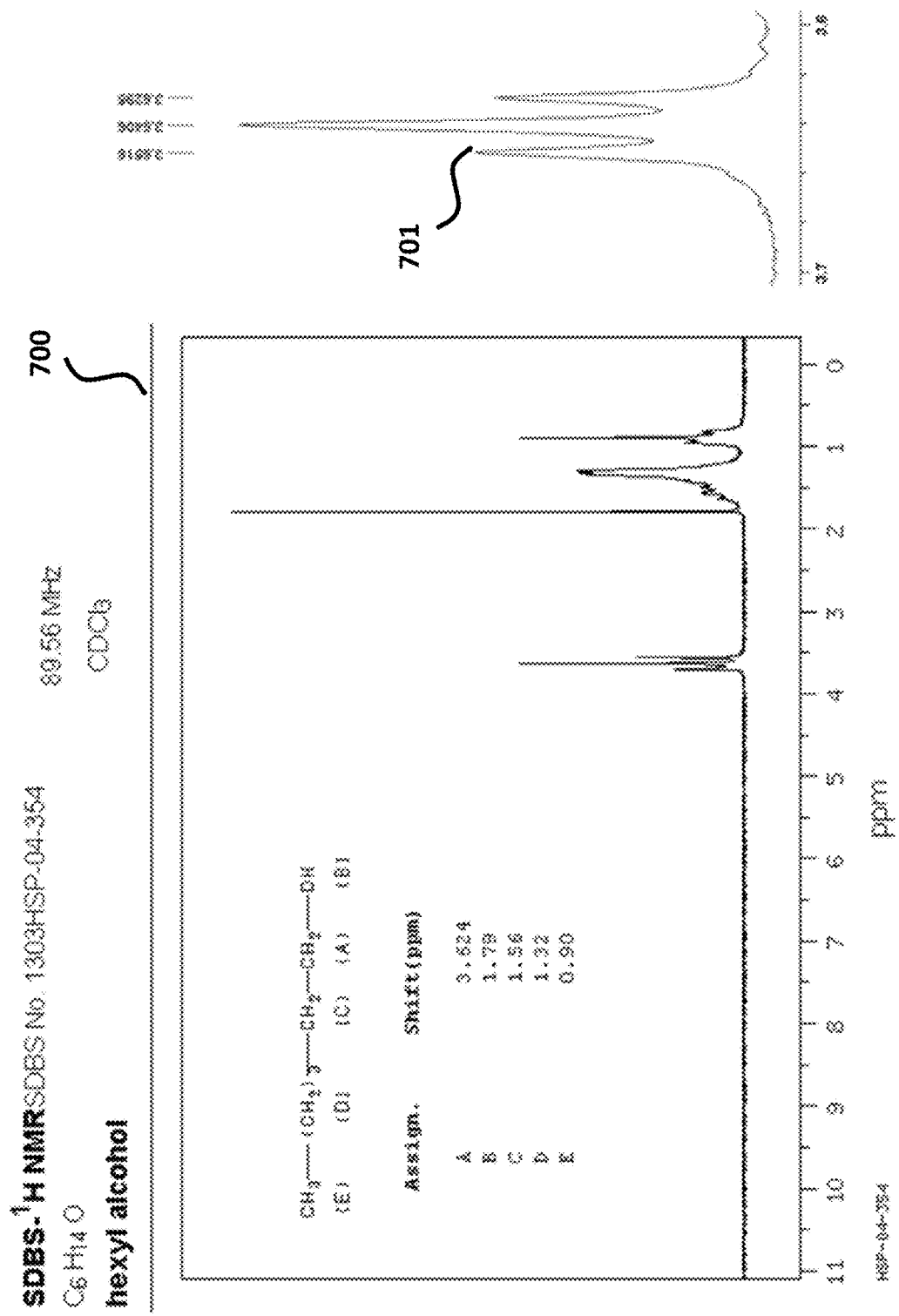
FIG. 7: is a reference spectra for 1-Hexanol and signature peak (triplet, 3.62/3.64)
Figure 8:
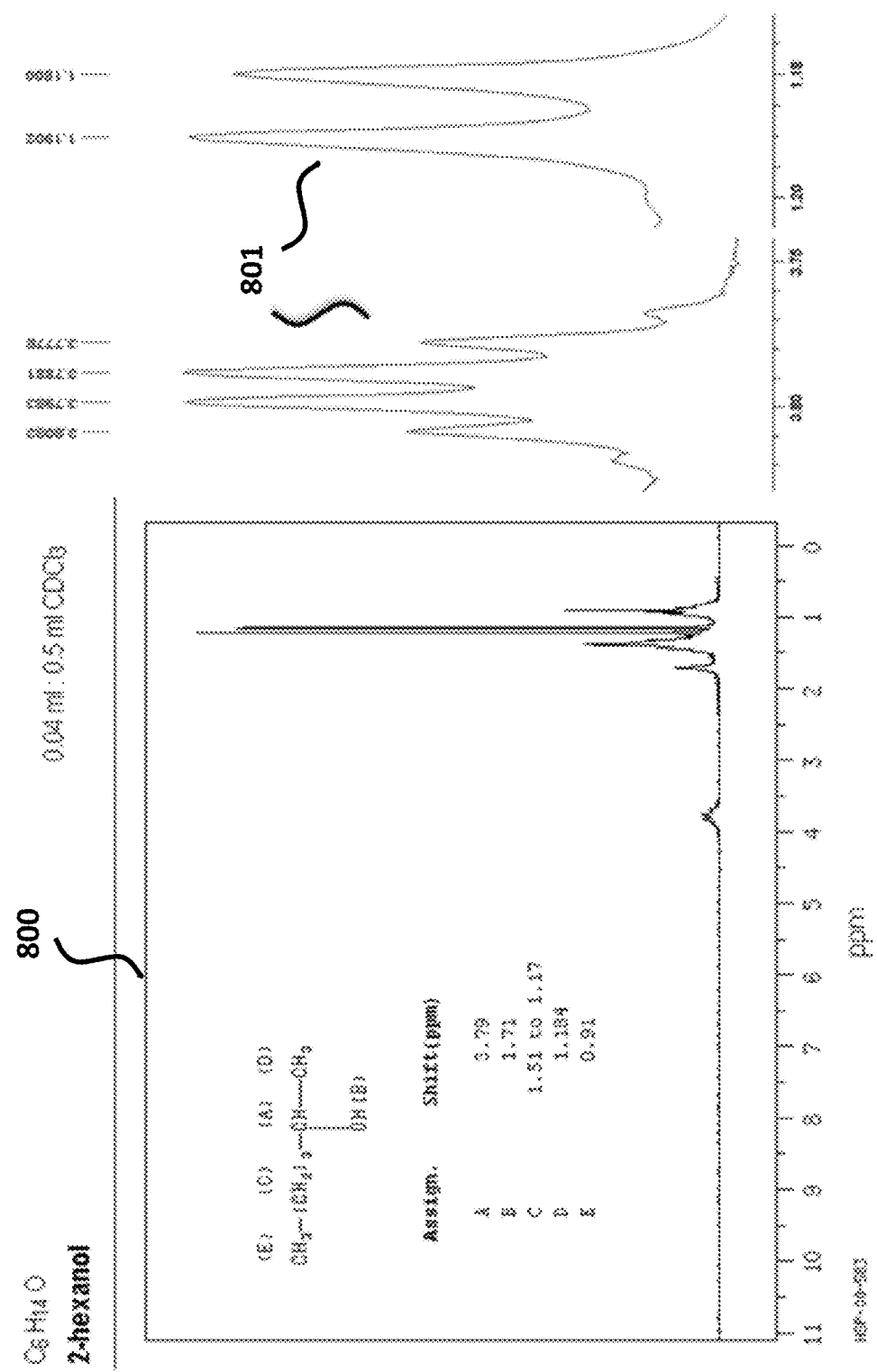
FIG. 8: is a reference spectra for 2-hexanol and signature peaks (multiplet, 3.79, doublet 1.18)
Figure 9:
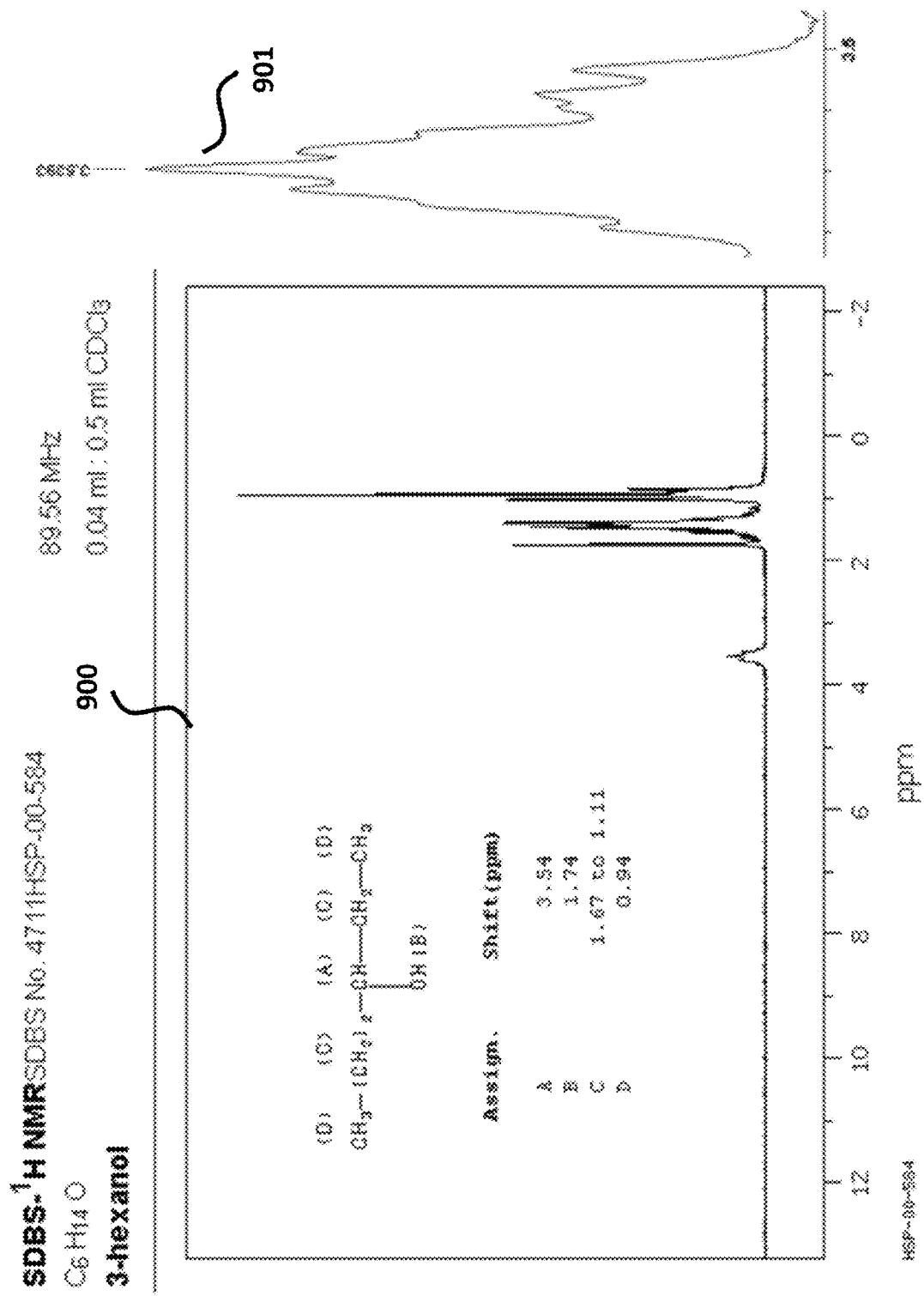
FIG. 9: is a reference spectra for 3-hexanol and signature peak (multiplet, 3.54)
Figure 10:
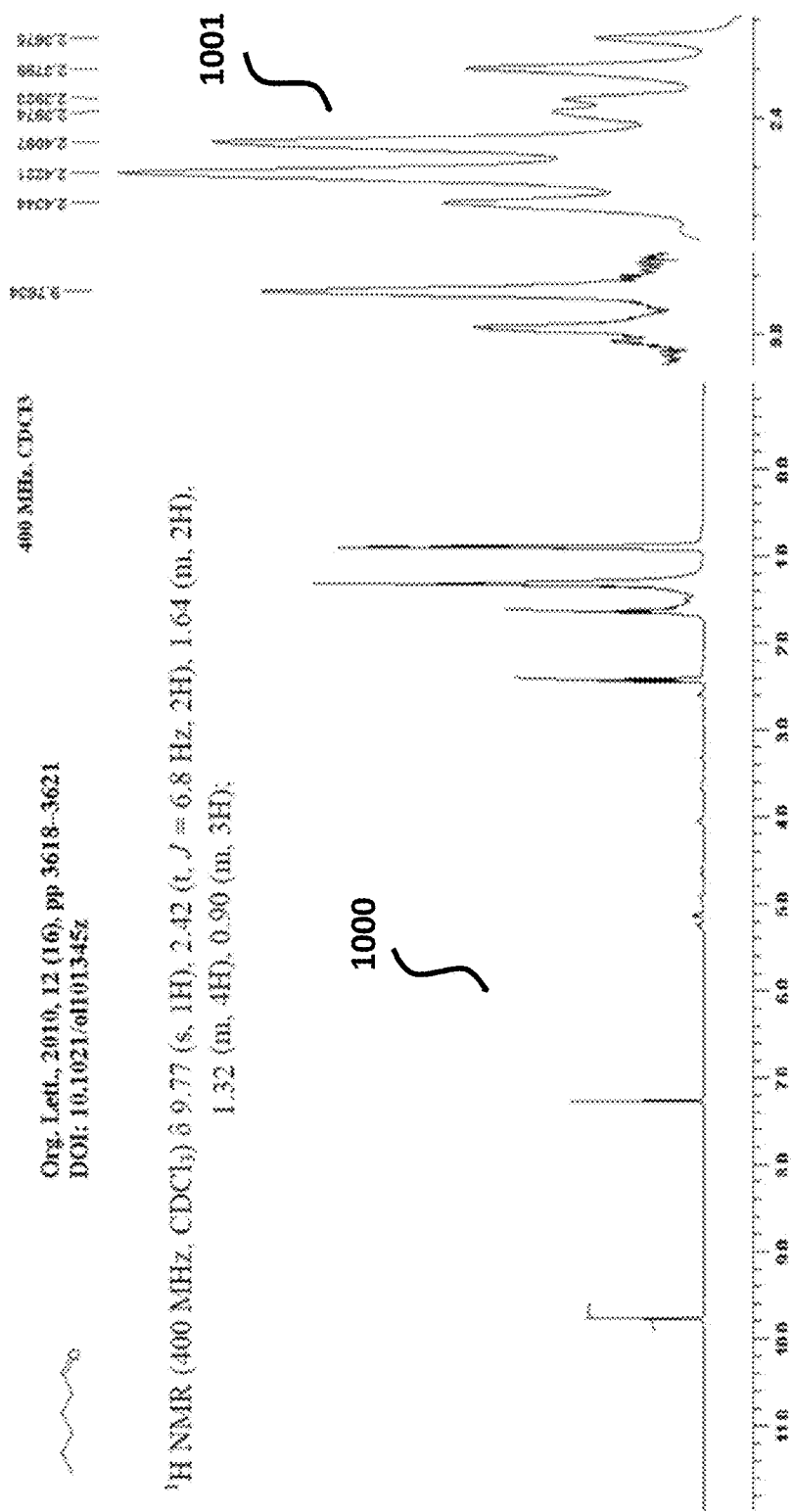
FIG. 10: is a reference spectra for hexanal and signature peaks (singlet, 9.77, triplet 2.42 merged with quartet)
Figure 11:
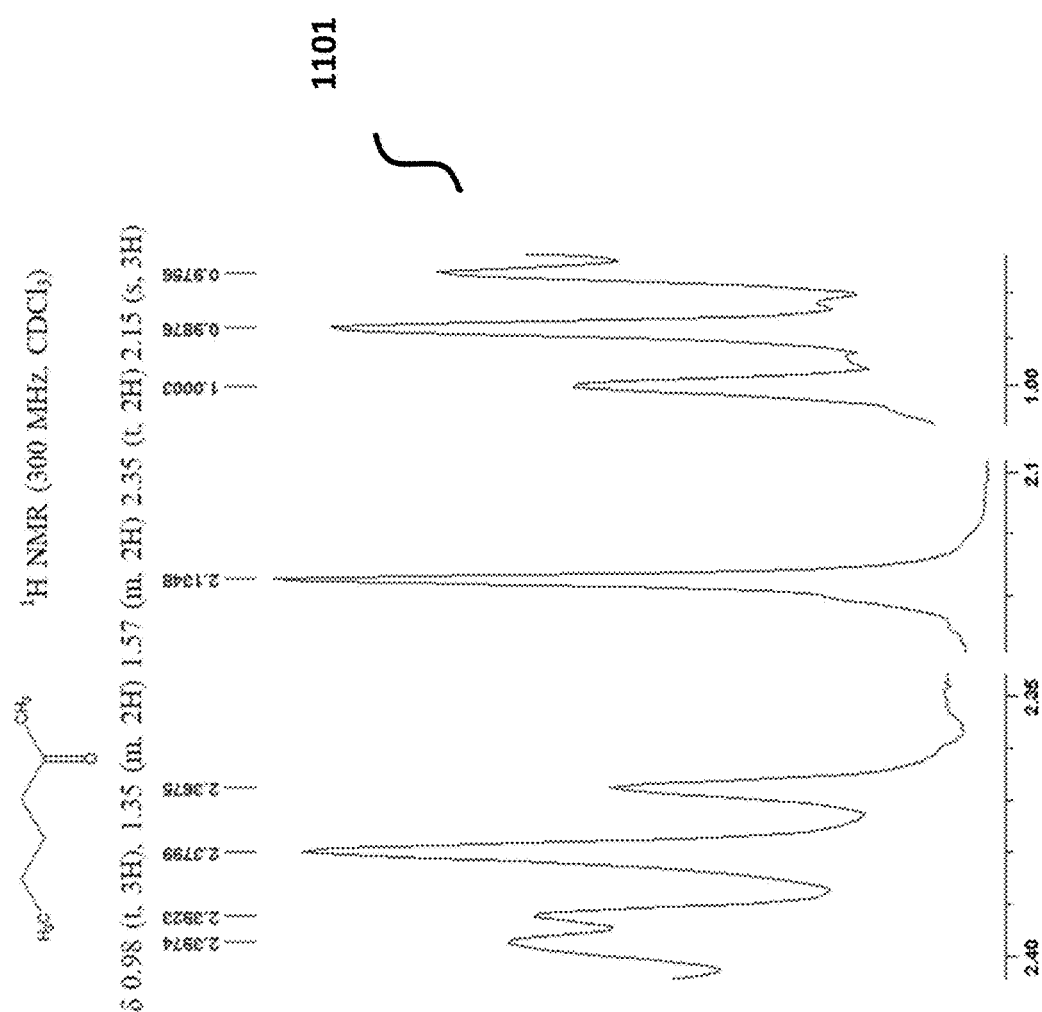
FIG. 11: shows reference shifts for 2-hexanone and signature peaks (triplet 0.98, singlet 2.15, triplet 2.35/2.38)
Figure 12:
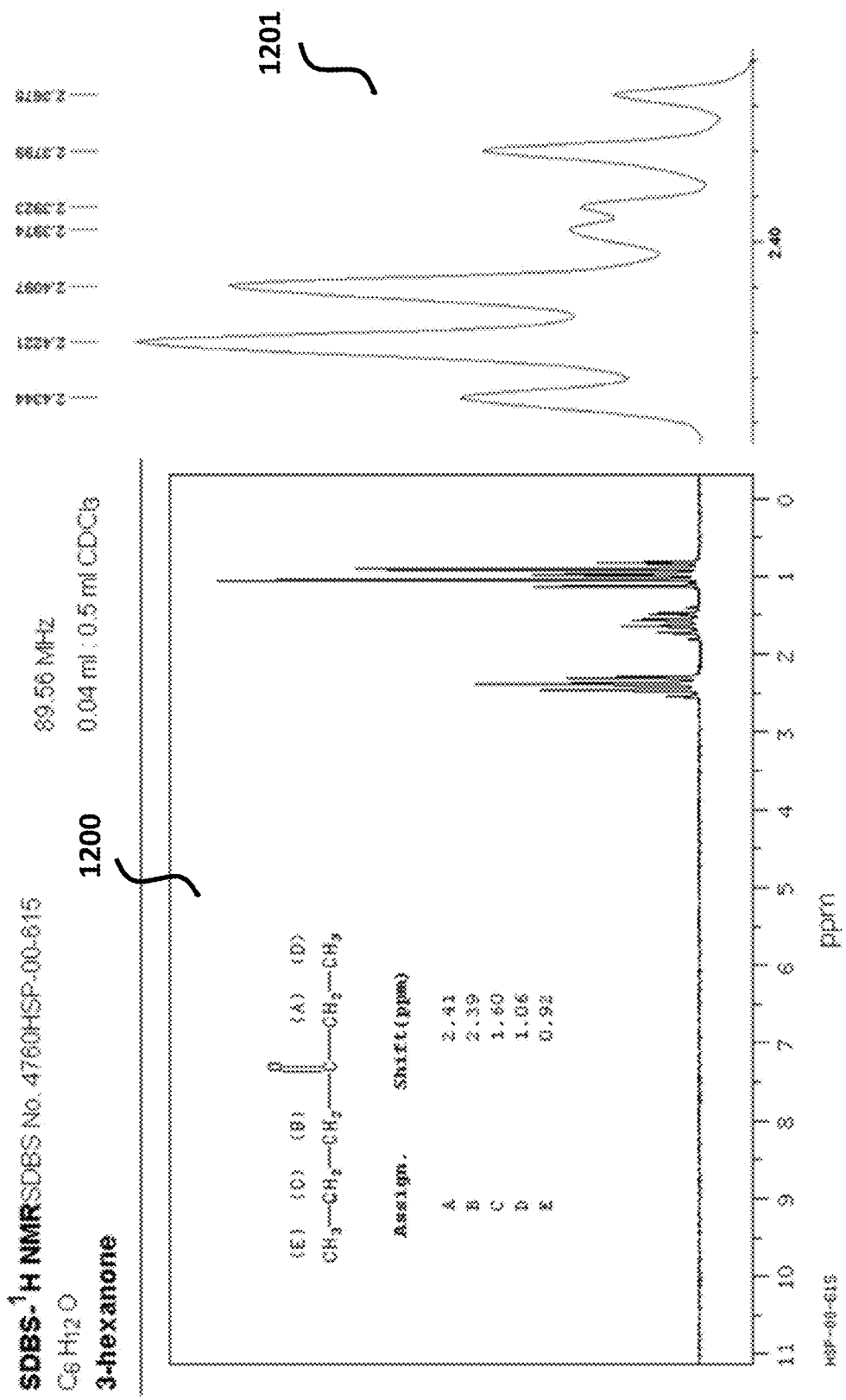
FIG. 12: is a reference spectra for 3-hexanone and signature peaks (quartet 2.41, triplet 2.39 merged)
Figure 13:
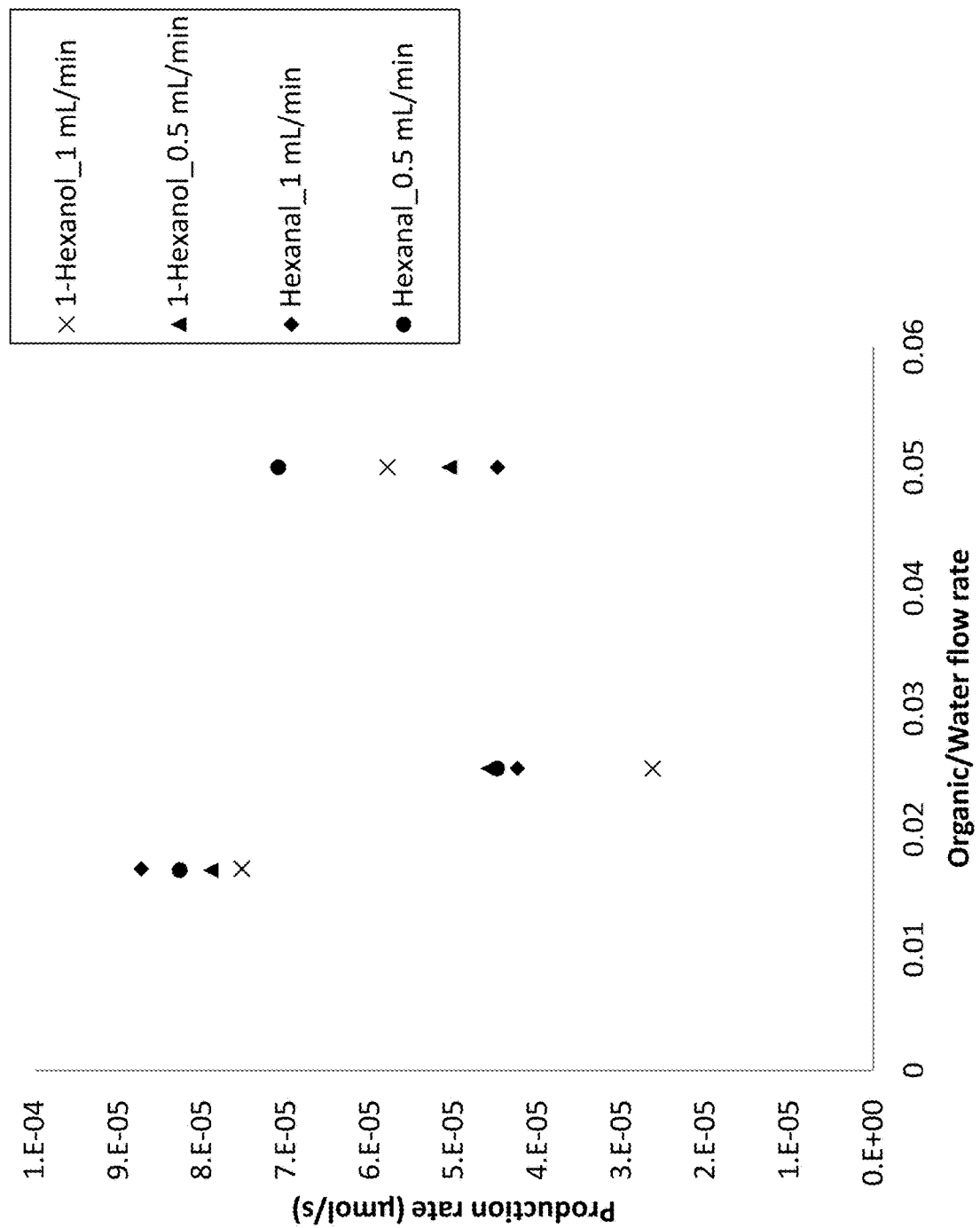
FIG. 13: is a chart showing production rates for 1-hexanol and hexanal as functions of feed flow rates.
Figure 14:
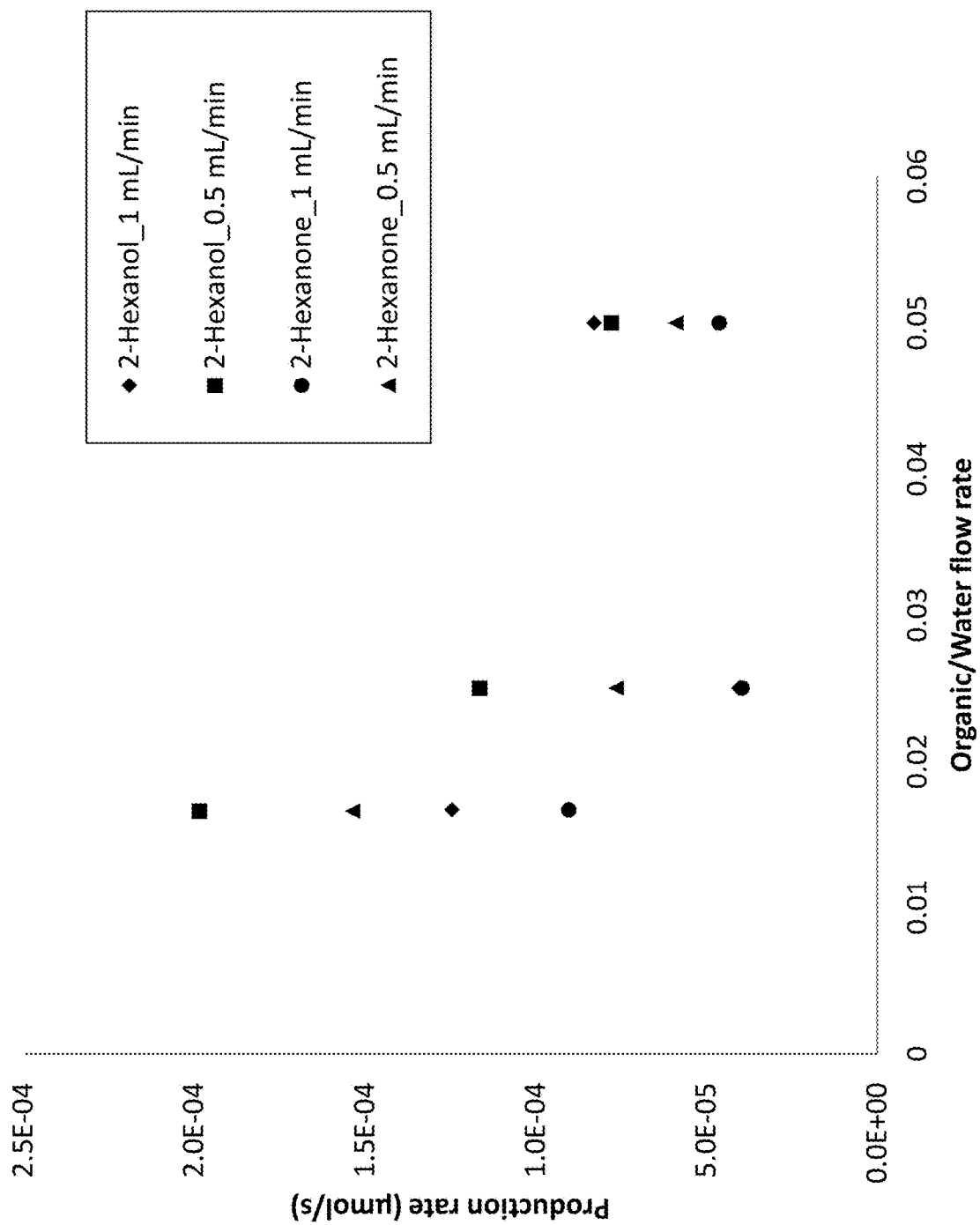
FIG. 14: is a chart showing production rates for 2-hexanol and 2-hexanone as functions of feed flow rates.
Figure 15:
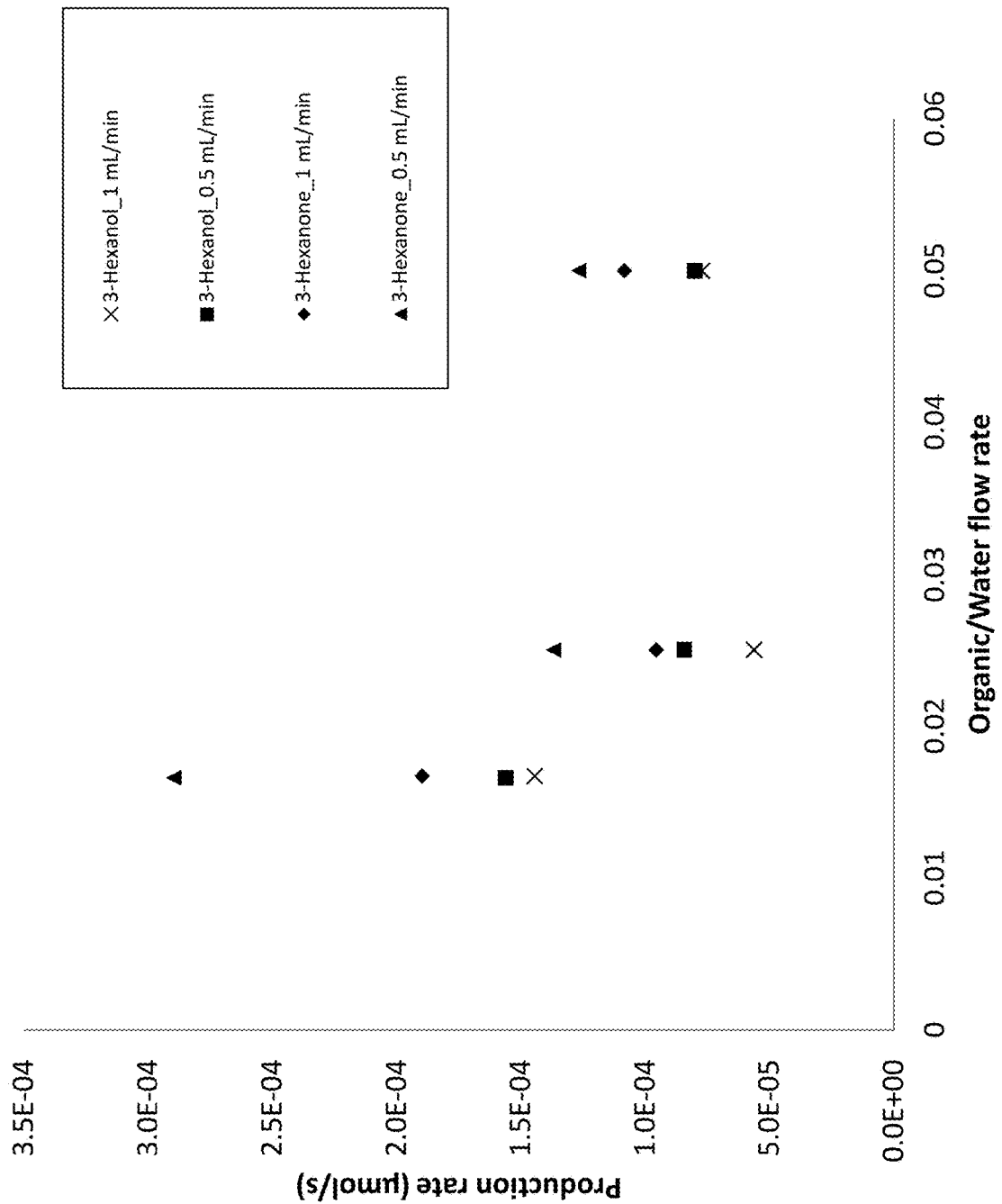
FIG. 15: is a chart showing production rates for 3-hexanol and 3-hexanone as functions of feed flow rates.

FIG. 7 shows the formation of 1-hexanol (blue from our reactor) by comparison of the triplet signature peaks 701 centered around 3.64 ppm with the reference spectra 700 taken from the literature. FIG. 8 shows a reference spectra 800 and experimental peaks 801 showing formation of 2-hexanol. FIG. 9 shows a reference spectra 900 and an experimental peak 901 showing formation of 3-hexanol. FIG. 10 shows a reference spectra 1000 and experimental peaks 1001 showing formation of the aldehyde, hexanal. FIG. 11 shows experimental peaks 1101 showing formation of the ketone, 2-hexanone. FIG. 12 shows a reference spectra 1200 and experimental peaks 1201 showing formation of the ketone, 3-hexanone.

Tables 1 through 6 show the concentrations, production rates, and energy yields for all six identified species for various inlet flow rates and ratios of organic to water in the feed. Typically the highest production rates and energy yields occur at the lower organic to water flow rate ratio (1.7E-2) for the cases with water flow rates of 0.5 ml/min, although for some cases the differences between water flow rates of 0.5 and 1 ml/min are minor. Generally the production rates and energy yields decrease as the ratio of organic to water flow rate increases, although for some cases the values are lowest for intermediate ratios of organic to water.

TABLE 1

| Water flow rate (mL/min) | Organic flow rate (mL/min) | Ratio organic/water | Conc. (M) | Conc. (mM) | Production Rate (umol/s) | Power (W) | Energy yield (mmol/kWh) |
|---|---|---|---|---|---|---|---|
| 5.00E−01 | 8.30E−03 | 1.66E−02 | 9.48E−06 | 9.48E−03 | 7.90E−05 | 1.5 | 1.90E−01 |
| 5.00E−01 | 1.25E−02 | 2.50E−02 | 5.51E−06 | 5.51E−03 | 4.59E−05 | 1.5 | 1.10E−01 |
| 5.00E−01 | 2.50E−02 | 5.00E−02 | 6.06E−06 | 6.06E−03 | 5.05E−05 | 1.5 | 1.21E−01 |
| 1.00E+00 | 1.67E−02 | 1.67E−02 | 4.52E−06 | 4.52E−03 | 7.53E−05 | 1.5 | 1.81E−01 |
| 1.00E+00 | 2.50E−02 | 2.50E−02 | 1.58E−06 | 1.58E−03 | 2.63E−05 | 1.5 | 6.32E−02 |
| 1.00E+00 | 5.00E−02 | 5.00E−02 | 3.48E−06 | 3.48E−03 | 5.80E−05 | 1.5 | 1.39E−01 |
| 2.50E−01 | 2.50E−03 | 1.00E−02 |  | 0.00E+00 | 0.00E+00 | 1.5 | 0.00E+00 |
| 2.50E−01 | 4.10E−03 | 1.64E−02 |  | 0.00E+00 | 0.00E+00 | 1.5 | 0.00E+00 |

TABLE 2

| Water flow rate (mL/min) | Organic flow rate (mL/min) | Ratio organic/water | Conc. (M) | Conc. (mM) | Production Rate (umol/s) | Power (W) | Energy yield (mmol/kWh) |
|---|---|---|---|---|---|---|---|
| 5.00E−01 | 8.30E−03 | 1.66E−02 | 2.38E−05 | 2.38E−02 | 1.98E−04 | 1.5 | 4.76E−01 |
| 5.00E−01 | 1.25E−02 | 2.50E−02 | 1.40E−05 | 1.40E−02 | 1.16E−04 | 1.5 | 2.79E−01 |
| 5.00E−01 | 2.50E−02 | 5.00E−02 | 9.34E−06 | 9.34E−03 | 7.78E−05 | 1.5 | 1.87E−01 |
| 1.00E+00 | 1.67E−02 | 1.67E−02 | 7.47E−06 | 7.47E−03 | 1.24E−04 | 1.5 | 2.99E−01 |
| 1.00E+00 | 2.50E−02 | 2.50E−02 | 2.42E−06 | 2.42E−03 | 4.04E−05 | 1.5 | 9.69E−02 |
| 1.00E+00 | 5.00E−02 | 5.00E−02 | 4.97E−06 | 4.97E−03 | 8.29E−05 | 1.5 | 1.99E−01 |
| 2.50E−01 | 2.50E−03 | 1.00E−02 |  | 0.00E+00 | 0.00E+00 | 1.5 | 0.00E+00 |
| 2.50E−01 | 4.10E−03 | 1.64E−02 |  | 0.00E+00 | 0.00E+00 | 1.5 | 0.00E+00 |
| 5.00E−01 | 2.50E−02 | 5.00E−02 | 9.34E−06 | 9.34E−03 | 7.78E−05 | 1.5 | 1.87E−01 |
| 1.00E+00 | 1.67E−02 | 1.67E−02 | 7.47E−06 | 7.47E−03 | 1.24E−04 | 1.5 | 2.99E−01 |

TABLE 3

| Water flow rate (mL/min) | Organic flow rate (mL/min) | Ratio organic/water | Conc. (M) | Conc. (mM) | Production Rate (umol/s) | Power (W) | Energy yield (mmol/kWh) |
|---|---|---|---|---|---|---|---|
| 5.00E−01 | 8.30E−03 | 1.66E−02 | 1.87E−05 | 1.87E−02 | 1.56E−04 | 1.5 | 3.75E−01 |
| 5.00E−01 | 1.25E−02 | 2.50E−02 | 1.01E−05 | 1.01E−02 | 8.43E−05 | 1.5 | 2.02E−01 |
| 5.00E−01 | 2.50E−02 | 5.00E−02 | 9.59E−06 | 9.59E−03 | 7.99E−05 | 1.5 | 1.92E−01 |
| 1.00E+00 | 1.67E−02 | 1.67E−02 | 8.67E−06 | 8.67E−03 | 1.44E−04 | 1.5 | 3.47E−01 |
| 1.00E+00 | 2.50E−02 | 2.50E−02 | 3.37E−06 | 3.37E−03 | 5.62E−05 | 1.5 | 1.35E−01 |
| 1.00E+00 | 5.00E−02 | 5.00E−02 | 4.63E−06 | 4.63E−03 | 7.72E−05 | 1.5 | 1.85E−01 |
| 2.50E−01 | 2.50E−03 | 1.00E−02 |  | 0.00E+00 | 0.00E+00 | 1.5 | 0.00E+00 |
| 2.50E−01 | 4.10E−03 | 1.64E−02 |  | 0.00E+00 | 0.00E+00 | 1.5 | 0.00E+00 |

TABLE 4

| Water flow rate (mL/min) | Organic flow rate (mL/min) | Ratio organic/water | Conc. (M) | Conc. (mM) | Production Rate (umol/s) | Power (W) | Energy yield (mmol/kWh) |
|---|---|---|---|---|---|---|---|
| 5.00E−01 | 8.30E−03 | 1.66E−02 | 9.92E−06 | 9.92E−03 | 8.26E−05 | 1.5 | 1.98E−01 |
| 5.00E−01 | 1.25E−02 | 2.50E−02 | 5.38E−06 | 5.38E−03 | 4.48E−05 | 1.5 | 1.08E−01 |
| 5.00E−01 | 2.50E−02 | 5.00E−02 | 8.51E−06 | 8.51E−03 | 7.09E−05 | 1.5 | 1.70E−01 |
| 1.00E+00 | 1.67E−02 | 1.67E−02 | 5.24E−06 | 5.24E−03 | 8.73E−05 | 1.5 | 2.10E−01 |
| 1.00E+00 | 2.50E−02 | 2.50E−02 | 2.54E−06 | 2.54E−03 | 4.24E−05 | 1.5 | 1.02E−01 |
| 1.00E+00 | 5.00E−02 | 5.00E−02 | 2.69E−06 | 2.69E−03 | 4.48E−05 | 1.5 | 1.07E−01 |
| 2.50E−01 | 2.50E−03 | 1.00E−02 |  | 0.00E+00 | 0.00E+00 | 1.5 | 0.00E+00 |
| 2.50E−01 | 4.10E−03 | 1.64E−02 |  | 0.00E+00 | 0.00E+00 | 1.5 | 0.00E+00 |

TABLE 5

| Water flow rate (mL/min) | Organic flow rate (mL/min) | Ratio organic/water | Conc. (M) | Conc. (mM) | Production Rate (umol/s) | Power (W) | Energy yield (mmol/kWh) |
|---|---|---|---|---|---|---|---|
| 5.00E−01 | 8.30E−03 | 1.66E−02 | 1.84E−05 | 1.84E−02 | 1.54E−04 | 1.5 | 3.69E−01 |
| 5.00E−01 | 1.25E−02 | 2.50E−02 | 9.18E−06 | 9.18E−03 | 7.65E−05 | 1.5 | 1.84E−01 |
| 5.00E−01 | 2.50E−02 | 5.00E−02 | 7.07E−06 | 7.07E−03 | 5.89E−05 | 1.5 | 1.41E−01 |
| 1.00E+00 | 1.67E−02 | 1.67E−02 | 5.42E−06 | 5.42E−03 | 9.03E−05 | 1.5 | 2.17E−01 |
| 1.00E+00 | 2.50E−02 | 2.50E−02 | 2.37E−06 | 2.37E−03 | 3.95E−05 | 1.5 | 9.48E−02 |
| 1.00E+00 | 5.00E−02 | 5.00E−02 | 2.77E−06 | 2.77E−03 | 4.61E−05 | 1.5 | 1.11E−01 |
| 2.50E−01 | 2.50E−03 | 1.00E−02 | | 0.00E+00 | 0.00E+00 | 1.5 | 0.00E+00 |
| 2.50E−01 | 4.10E−03 | 1.64E−02 | | 0.00E+00 | 0.00E+00 | 1.5 | 0.00E+00 |

TABLE 6

| Water flow rate (mL/min) | Organic flow rate (mL/min) | Ratio organic/water | Conc. (M) | Conc. (mM) | Production Rate (umol/s) | Power (W) | Energy yield (mmol/kWh) |
|---|---|---|---|---|---|---|---|
| 5.00E−01 | 8.30E−03 | 1.66E−02 | 3.48E−05 | 3.48E−02 | 2.90E−04 | 1.5 | 6.95E−01 |
| 5.00E−01 | 1.25E−02 | 2.50E−02 | 1.64E−05 | 1.64E−02 | 1.37E−04 | 1.5 | 3.29E−01 |
| 5.00E−01 | 2.50E−02 | 5.00E−02 | 1.52E−05 | 1.52E−02 | 1.27E−04 | 1.5 | 3.04E−01 |
| 1.00E+00 | 1.67E−02 | 1.67E−02 | 1.14E−05 | 1.14E−02 | 1.90E−04 | 1.5 | 4.55E−01 |
| 1.00E+00 | 2.50E−02 | 2.50E−02 | 5.74E−06 | 5.74E−03 | 9.56E−05 | 1.5 | 2.30E−01 |
| 1.00E+00 | 5.00E−02 | 5.00E−02 | 6.50E−06 | 6.50E−03 | 1.08E−04 | 1.5 | 2.60E−01 |
| 2.50E−01 | 2.50E−03 | 1.00E−02 | | 0.00E+00 | 0.00E+00 | 1.5 | 0.00E+00 |
| 2.50E−01 | 4.10E−03 | 1.64E−02 | | 0.00E+00 | 0.00E+00 | 1.5 | 0.00E+00 |

Figure 16:
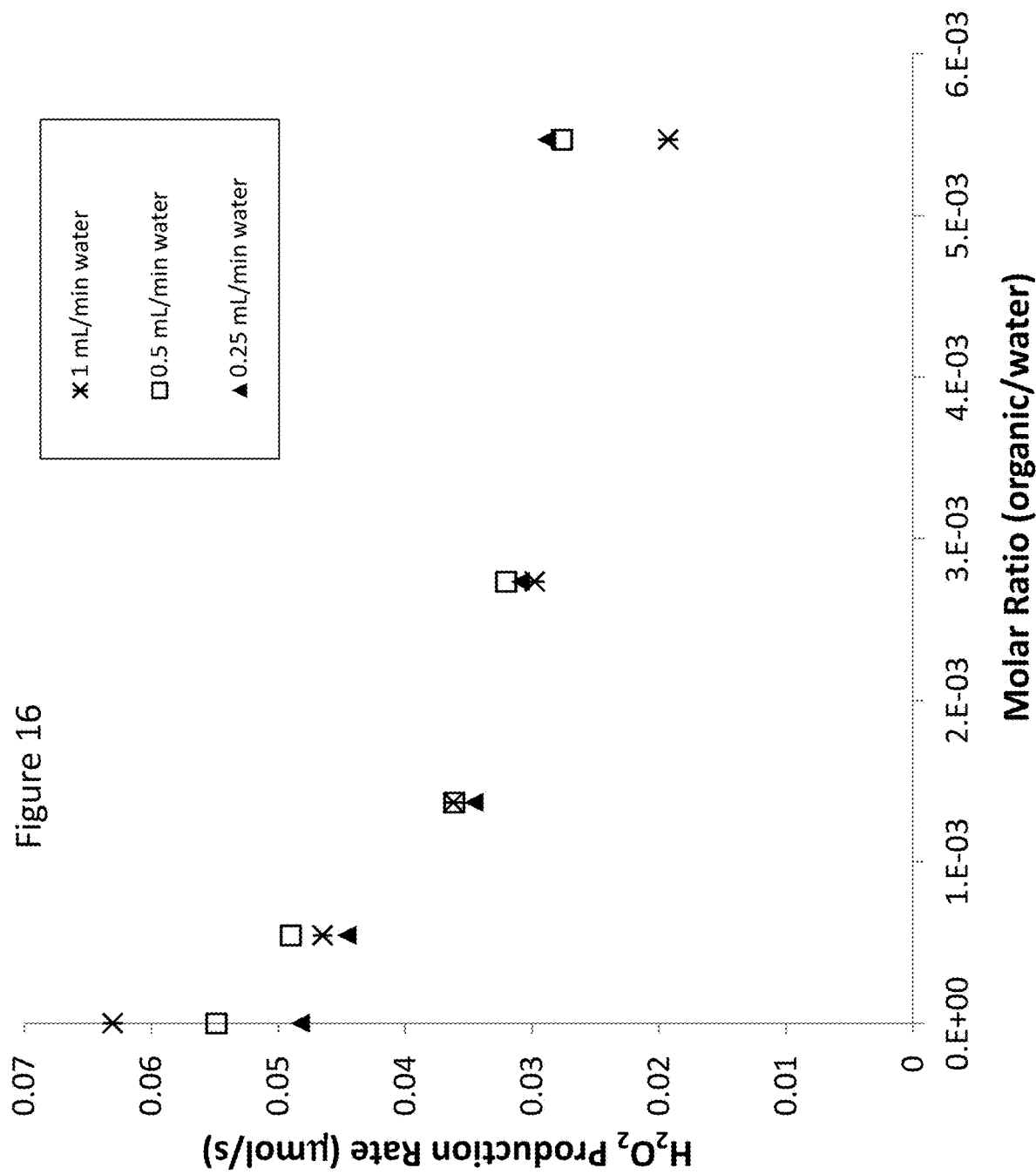
FIG. 16: is a chart showing formation rate of hydrogen peroxide as a function of the organic content in the feed for various liquid water flow rates.

FIGS. 13 to 16 show the production rates as functions of the ratio of organic to water flow rates for the alcohols, aldehydes, and ketones. Clearly variation of the relative flow rates of the hexane and water affect the production rate and lower ratios of hexane to water lead to higher production rates of the organic products. The OH radical appears to preferentially attack the tertiary carbon as indicated by the higher production rates of 3-hexanol and 3-hexanal in comparison to the primary and secondary compounds. The preferential attack on the tertiary carbon is consistent with that seen in oxygen plasma reactions with hexane. FIG. 16 shows the production rate of hydrogen peroxide as functions of the organic content in the feed for various liquid water flow rates. Clearly, as the amount of organic increases relative to that of water, the amount of hydrogen peroxide measured in the liquid phase decreases. This is likely due to the competing reaction of OH radicals with the organic relative to the recombination of the OH radical to form hydrogen peroxide. Clearly, significant hydrogen peroxide persists even in the presence of relatively large amounts of organic compound and higher concentrations of hydrogen peroxide occur with lower water flow rates and this latter finding is consistent with our previous work in the absence of hexane addition. The production rate of hydrogen peroxide is not largely affected by the presence of the organic compound except at very large molar ratios of organic to water.

Figure 18:
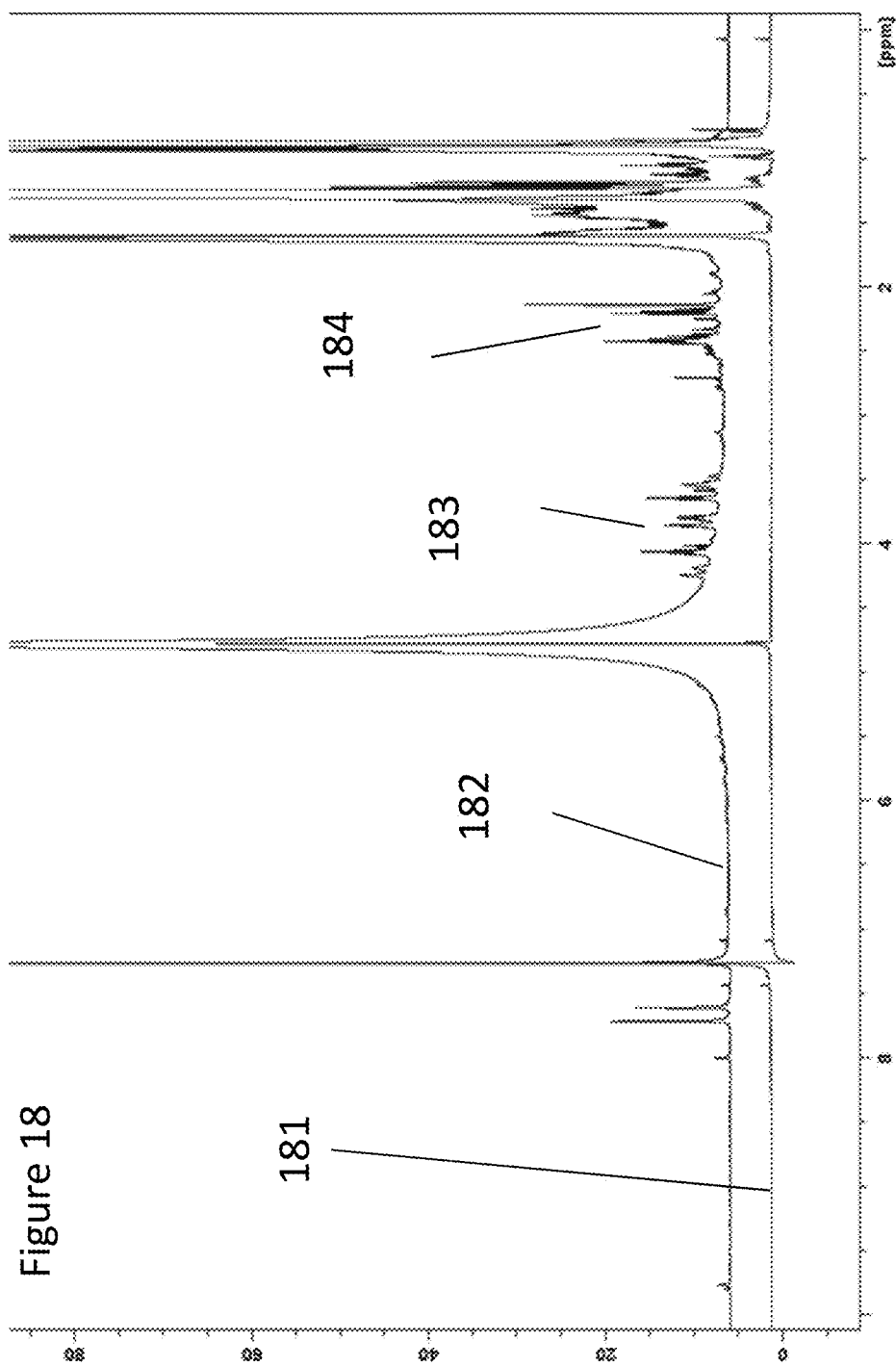
FIG. 18 shows complete NMR-spectra of liquid effluent after extraction, the bottom spectrum representing the starting material (DI water and n-hexane), the top spectrum representing the sample after subjection to plasma discharge.

FIG. 18 shows an example NMR spectrum demonstrating the presence of reaction products from n-hexane. In this figure the bottom spectrum represents the unreacted starting material while the top spectrum represents the liquid effluent from the reactor after extraction. Comparison of these clearly shows the presence of both alcohol and ketone products in the characteristic regions of the functional groups. The major products and their relative ratios as identified with NMR were 3-hexanol (26%), 2-hexanol (21%), 3-hexanone (17%) and 2-hexanone (17%), 1-hexanol (11%), hexanal (8%). A significant amount of unreacted n-hexane was also found. Additionally, the NMR analysis also suggests the presence of organic peroxides; however they could not be reliable assigned due to the relatively low stability. The NMR spectrum shows a starting material spectrum 181, corresponding to n-hexane and DI water; a product spectrum 182; an alcohol region 183; and a ketone region 184.

Figure 19:
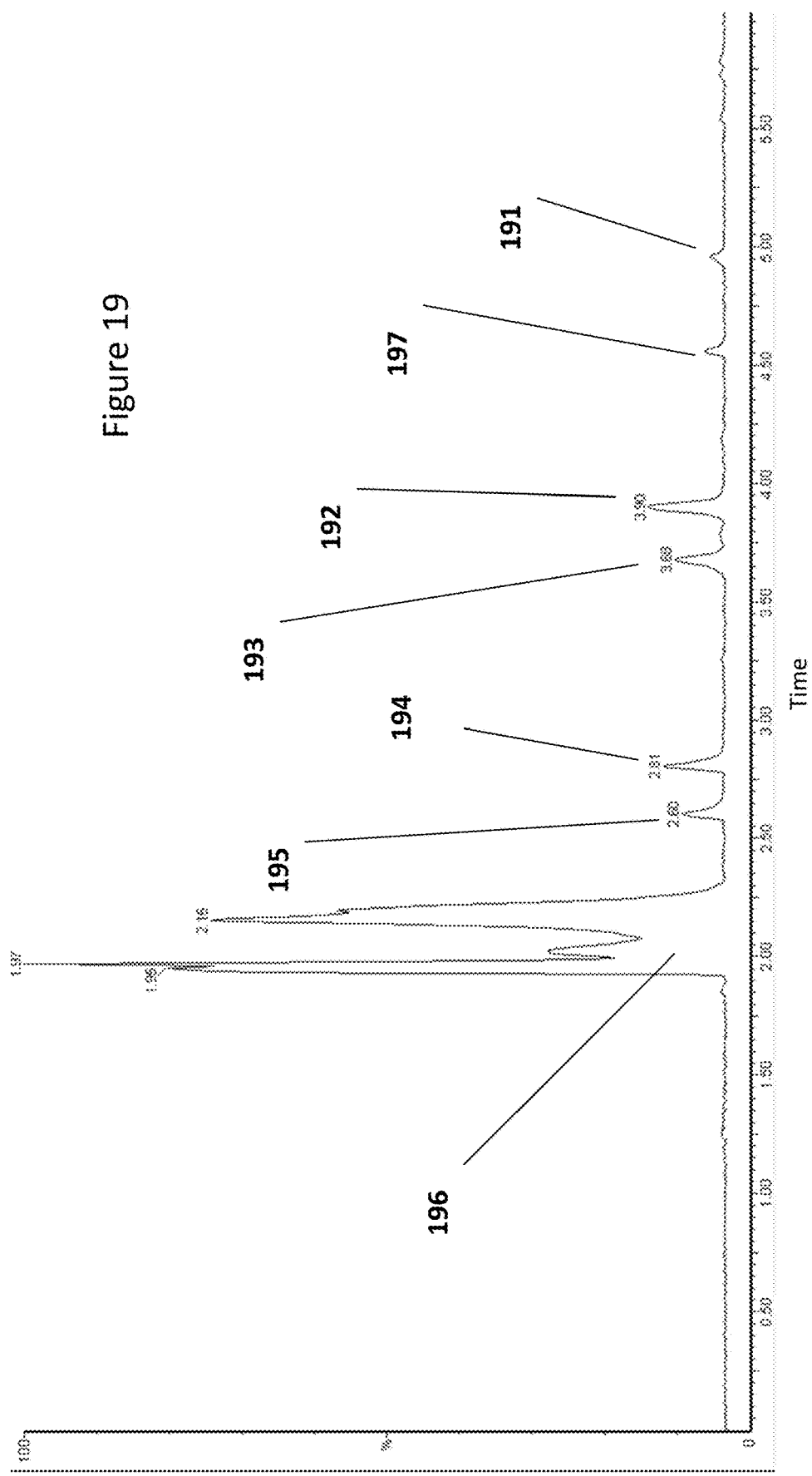
FIG. 19 shows complete gas chromatogram of liquid effluent after extraction and solvent evaporation, where the products identified are 1-hexanol (4.95 min), 2-hexanol (3.90 min), 3-hexanol (3.68 min), hexanal (2.81 min), 2-hexanone (2.81 min), and 3-hexanone (2.60 min)

FIG. 19 depicts a gas chromatogram of the reaction products from n-hexane. As with the NMR analysis the main products identified were 1-hexanol (4.95 min) 191, 2-hexanol (3.90 min) 192, 3-hexanol (3.68 min) 193, hexanal (2.81 min), 2-hexanone, hexanal (2.81 min) 194, and 3-hexanone (2.60 min) 195. A chloroform peak 196 and an unidentified peak 197 were also observed. It should be noted that separation of 2-hexanone from hexanal was not achieved and the two compounds appear as one peak. Further, an additional peak appears at 4.52 min which could not been identified but may be accounted for by the suggested presence of organic peroxides given in the NMR analysis.

A similar analysis was performed in order to assess the products generated when cyclohexane was used as the organic feedstock instead of n-hexane. A comparison of the major product distributions of the two experiments can be found in Table 7. More specifically, Table 7 shows major product distribution of the compounds formed from n-hexane (top) and cyclohexane (bottom) as well as percent conversion, overall production rate, and energy yield. All values presented on are on a per mole bases.

TABLE 7

| Mole percent conversion of organic | Mole percent of unreacted organic collected | Total organic product production rate (μmol/hr) | Total organic product energy yield (mmol/ kWh) | Major product distribution | |
|---|---|---|---|---|---|
| n-hexane | | | | | |
| 1.7% | 9.8% | 15.4 | 30.8 | 3-Hexanol | 26% |
| | | | | 2-Hexanol | 21% |
| | | | | 3-Hexanone | 17% |
| | | | | 2-Hexanone | 17% |
| | | | | 1-Hexanol | 11% |
| | | | | Hexanal | 8% |
| Cyclohexane | | | | | |
| 1.7% | 21.9% | 16.2 | 32.5 | Cyclohexanone | 47% |
| | | | | Cyclohexene | 20% |
| | | | | Cyclohexanol | 19% |
| | | | | Hexanal | 11% |
| | | | | 2-cyclohexenone | 2% |

When cyclohexane was utilized as the organic starting material the major products identified and their relative distributions were cyclohexanone (47%), cyclohexene (20%), cyclohexanol (19%), hexanal (11%), and 2-cyclohexenone (2%). As with the conversion of n-hexane, NMR analysis also suggests the presence of organic peroxides (i.e., $C_6H_{11}OOH$) derived from cyclohexane. In both experiments only a small fraction of the organic starting material was functionalized, 1.7%. for n-hexane and 2.0% for cyclohexane. While this is a small fraction it should be noted that a large portion of the organic starting material not accounted for in the form of functionalized products does not undergo further oxidation but instead remains unreacted. This is evident from the significant amount of unreacted organic feed detected in the NMR analysis; unfortunately, accurate quantification of these compounds was not possible due to the overlap of the compound's NMR signals with the NMR signals for the aliphatic parts of the products. None the less, a rough quantification was determined showing approximately 10% of the n-hexane starting material was collected and 22% for cyclohexane. It should be noted that additional organic starting material was detected in the gas effluent after passage through both cold traps, and likely accounts for a large fraction of organic starting material not collected, but could not be quantified with the instrumentation available. The fact that only a portion of the starting material was chemically modified and that most of the products generated were the result of only one or two oxidative steps of the parent molecule indicates that our reactor system provides soft activation, thus justifying the viability of this set up for potential chemical synthesis routes in partial oxidation of the alkanes.

When the distribution of products generated from the oxidation of n-hexane is examined, the OH radical appears to preferentially attack the $C_2$ and $C_3$ carbons of the n-hexane molecule as indicated by the lower ratios of 1-hexanol and hexanal in comparison to the ketones and secondary alcohols. This preferential attack is consistent with data reported in the literature for oxygen plasma reactions with n-hexane in DBD.

When the distribution of the products generated from the oxidation of cyclohexane is examined it is clear that reaction selectivity is higher when compared to the oxidation of n-hexane as evident from the large portion of cyclohexanone, 47%, found relative to the other products. The fact that there is no distinction between carbons in the cyclohexane molecule likely leads to this increase in selectivity. However, it is not clear why the ketone product dominates when cyclohexane is utilized while the alcohols dominate in the case of n-hexane. This result differs from those found when cyclohexane was oxidized with oxygen in DBD where an almost equal ratio of cyclohexanone to cyclohexanol was produced. It should additionally be pointed out that the generation of cyclohexene is likely to result from the loss of hydrogen atom from cyclohexyl radical. It is known that β-C—H bond energy in the alkyl radicals is nearly a factor of 3 smaller than that in respective alkanes. Further, this product was not reported in the above mentioned studies with oxygen in DBD.

The overall production rate and energy yield for the major products generated are also given in Table 7. The energy yield for products generated from n-hexane was found to be $8.6 \times 10^{-9}$ mol/J and $9.0 \times 10^{-9}$ mol/J for cyclohexane. These values are approximately an order of magnitude lower than those found for the degradation of n-hexane and cyclohexane by oxygen plasma reactions in DBD where the authors reported $1.1 \times 10^{-7}$ and $1.9 \times 10^{-7}$ mol/J respectively. However, it should be noted that this does not represent the total energy yield for all generated products because hydrogen peroxide is also produced at an energy yield of 0.54 mol/kWh ($1.5 \times 10^{-7}$ mol/J).

Table 8 shows the individual production rates and energy yields for all products generated in the experiments. More specifically, Table 8 shows individual production rates and energy yields for the generated products produced as well as the relative distribution of where the products were collected. All values presented are on a per mole bases.

TABLE 8

| Compound | Production rate (μmol/ hr) | Energy yield (mmol/ kWh) | Mole percent collected in liquid effluent | Mole percent collected in primary cold trap | Mole Percent collected in secondary cold trap |
|---|---|---|---|---|---|
| n-hexane | | | | | |
| n-Hexane | n/a | n/a | 0% | 19% | 81% |
| 1-Hexanol | 1.6 | 3.3 | 48% | 22% | 31% |
| 2-Hexanol | 3.2 | 6.4 | 47% | 24% | 29% |
| 3-Hexanol | 4.0 | 8.1 | 44% | 20% | 36% |
| Hexanal | 1.3 | 2.5 | 38% | 17% | 45% |
| 2-Hexanone | 2.6 | 5.3 | 40% | 21% | 39% |
| 3-Hexanone | 2.7 | 5.3 | 32% | 27% | 41% |
| Hydrogen Peroxide | 273 | 545 | 100% | 0% | 0% |
| Cyclohexane | | | | | |
| Cyclohexane | n/a | n/a | 0% | 0% | 100% |
| Cyclohexene | 3.3 | 6.6 | 0% | 0% | 100% |
| Cyclohexanone | 7.6 | 15.2 | 54% | 14% | 32% |
| Cyclohexanol | 3.1 | 6.3 | 42% | 16% | 43% |
| Hexanal | 1.8 | 3.6 | 6% | 2% | 93% |
| 2-cyclohexenone | 0.4 | 0.8 | 80% | 9% | 11% |
| Hydrogen peroxide | 259 | 518 | 100% | 0% | 0% |

Table 8 also provides a breakdown of where the generated products were collected, i.e. the relative ratios of products in the three separate liquid fractions which were collected and extracted. One of the more important generalizations of Table 8 is that no n-hexane, cyclohexane, or cyclohexene was detected in the liquid effluent collection vessel and conversely no hydrogen peroxide was detected in either the primary or secondary cold traps. This result can be explained by the vastly different vapor pressures and water solubility of these organic compounds compared to hydrogen peroxide, in that the high water solubility of hydrogen peroxide as well its relativity low vapor pressure allow the product to be rapidly dissolved into the liquid water phase leaving no detectable amounts vaporized in the flowing argon gas. In contrast, the high volatility and low solubility in water of n-hexane, cyclohexane, and cyclohexene hinders them from dissolving into the liquid effluent making these compounds difficult to collect. As previously mentioned it is likely a significant amount of these volatile compounds is still present in the gas effluent of the secondary cold trap. This result demonstrates the importance of the relative chemical properties of the products of interest to those of the liquid absorbent, which is in this case water. Because the volatility and solubility of the other major products lies between the extremes of the previously mentioned organic compounds and hydrogen peroxide, these compounds are collected in both the liquid effluent and cold traps. As a result, it is reasonable to conclude that almost all of the hydrogen peroxide produced in the reactor is collected but a portion of the other organic products generated as well as a large amount of unreacted starting material may remain vaporized in the argon gas even after subjection to two cold traps. Our future experiments will determine whether it is possible to improve overall yield by choosing a parent compound whose oxidative products are more soluble in water and less volatile.

Additional experiments were conducted to determine the radical scavenging potential of increasing amounts of organic starting material in order to assess the impact on the production rate of hydrogen peroxide. In these experiments the water flow rate was held constant at 0.5 mL/min while the n-hexane flow rate was varied from 0 to 0.002, 0.005, 0.01, 0.02, and 0.04 mL/min. The values for hydrogen peroxide production rate as well as the discharge power under these conditions are shown in FIGS. 20a and 20b.

FIG. 20a shows that as the amount of n-hexane added to the reactor was increased, the power of the discharge also increased. FIG. 20b shows the production rate of hydrogen peroxide increased from the case with pure water when only a very small amount of n-hexane (0.002-0.005 mL/min) was added to the reactant feed. This increase can be explained by the slight increase in power that occurred when the n-hexane was added to the gas phase. The result also shows that when only a small amount of n-hexane is added to the reactant feed the hydroxyl radical reactions with the organic compounds do not affect the hydrogen peroxide formation rate. When this experiment was performed with cyclohexane as the organic starting material almost identical trends were found. It is possible that the hydroxyl radical reactions which produce the hydrogen peroxide occur very close to the liquid-gas interface, and thus are unaffected by gas phase organic radical scavengers at low enough concentration. This hypothesis is supported by the fact that when the ratio of organic to water was increased further, the production rate of hydrogen peroxide decreased even though the discharge power continued to increase. A similar finding, whereby increasing radical probe concentration reduced hydrogen peroxide formation, was found in a pulsed corona discharge directly in liquid water.

Lastly, there was no visual evidence of polymerization products in the present experiments further justifying that over oxidation was prevented. However, additional analysis of the gas effluent is necessary to determine if there is indeed additional product still vaporized in the argon and to quantify the remaining starting material in this phase in order to close the mass balance.

The results of this study clearly show that chemical synthesis by oxidation with hydroxyl radicals is possible with the reactor system described in this paper. Significant amounts of alcohol, ketone, and aldehyde products were produced from both n-hexane and cyclohexane after attack on the molecules by hydroxyl radicals produced from the liquid water phase contacting the plasma. This work also proves that some selectivity of the reaction products can be gained by the choice of a parent compound, and also suggests that it may be possible to further control selectivity with alterations to such experimental conditions as water flow rate, organic to water feed ratio, reactor pressure, and pulse parameters. Additionally, substantial amounts of hydrogen peroxide were also produced despite the addition of the organic compounds to the reactor feed which have been shown to act as gas phase radical scavengers at high enough concentrations. It was also found that the selection of a parent compound which yields chemical species with a low volatility and a high solubility in water upon oxidation could make collection of the generated products easier and increase the overall yield of the process. Finally, due to the high concentration of hydrogen peroxide produced in conjunction with the other major functionalized products, additional work is warranted to capitalize on this aspect of the system.

Although the present invention has been described in considerable detail with reference to certain preferred versions thereof, other versions are possible. Therefore, the spirit and scope of the appended claims should not be limited to the description of the preferred versions contained herein.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

What is claimed is:

1. A reactor comprising:
   a tubular reactor body portion having one or more internal walls that define an internal cavity;
   at least one electrically-conductive inlet capillary having an inlet capillary body extending between a fluid-receiving tip and a fluid-injecting tip, wherein the fluid-receiving tip is positioned outside the internal cavity, and wherein the fluid-injecting tip is positioned inside the internal cavity;
   at least one electrically-conductive outlet capillary having an outlet capillary body extending between a fluid-collecting tip and a fluid-ejecting tip, wherein the fluid-collecting tip is positioned inside the internal cavity, and wherein the fluid-ejecting tip is positioned outside the internal cavity, the inlet capillary being aligned with the outlet capillary;
   the electrically-conductive inlet capillary having a first internal diameter, the tubular reactor body having a second internal diameter, and the electrically conductive outlet capillary having a third internal diameter, the third internal diameter being larger than the first internal diameter and smaller than the second internal diameter;

a mixing chamber outside of the tubular reactor body having a gas inlet, a liquid inlet, and a mixed gas and liquid outlet, the mixed gas and liquid outlet being in fluid communication with the fluid-receiving tip of the electrically conductive inlet capillary;

a power source supplying a voltage across the at least one electrically-conductive inlet capillary and the at least one electrically-conductive outlet capillary;

wherein the fluid injecting tip is disposed relative to the fluid collecting tip to generate a flowing liquid film region on the one or more internal walls and a gas stream flowing through the flowing liquid film region, when a fluid is injected into the internal cavity via the at least one electrically conductive inlet capillary;

wherein the fluid injecting tip is disposed relative to the fluid collecting tip to propagate a plasma discharge along the flowing liquid film region between the at least one electrically-conductive inlet capillary and the at least one electrically-conductive outlet capillary.

2. The reactor according to claim 1, wherein the power source is adapted to provide a pulsed current between the at least one electrically-conductive inlet capillary and the at least one electrically-conductive outlet capillary.

3. The reactor according to claim 1, wherein the power source is adapted to provide a D.C. current between the at least one electrically-conductive inlet capillary and the at least one electrically-conductive outlet capillary.

4. The reactor according to claim 1, wherein the power source is adapted to provide an A.C. current between the at least one electrically-conductive inlet capillary and the at least one electrically-conductive outlet capillary.

5. The reactor according to claim 1, wherein a gap separates the fluid-injecting tip and the fluid-collecting tip, wherein the gap has a length, and wherein a ratio of the voltage to the length is at least about $2.5 \times 10^5$ V/m.

6. The reactor according to claim 1, wherein the body portion is cylindrical, wherein the body portion has a first diameter of from 1 mm to 1 cm, wherein the at least one electrically-conductive inlet capillary has a second diameter that is less than the first diameter, and wherein the at least one electrically-conductive outlet capillary has a third diameter that is greater than the second diameter and less than the first diameter.

7. A reactor system comprising:
an electrically-conductive inlet capillary tube electrode for simultaneously charging a liquid and gas inside the electrode, the electrically-conductive inlet capillary tube electrode having a first internal diameter;

a tubular plasma reactor having a second internal diameter and having one or more internal walls;

an electrically conductive outlet capillary tube electrode having a third internal diameter, the third internal diameter being larger than the first internal diameter and smaller than the second internal diameter, the inlet capillary being aligned with the outlet capillary;

a power source for supplying a voltage across the at least one electrically-conductive inlet capillary tube and the at least one electrically-conductive outlet capillary tube;

a mixing chamber outside of the tubular reactor having a gas inlet, a liquid inlet, and a mixed gas and liquid outlet, the mixed gas and liquid outlet being in fluid communication with the electrically-conductive inlet capillary tube electrode being configured to inject a charged mixture comprising a liquid and a gas into the plasma reactor, the injecting of the charged liquid and gas generating a continuously flowing liquid film region on one or more internal walls, and a gas stream flowing along the flowing liquid film region, the injecting further propagating a plasma discharge channel pattern along the interface between the flowing liquid film region and the flowing gas stream inside the plasma reactor.

8. The reactor system of claim 7, wherein the liquid comprises water and the reaction product comprises hydrogen peroxide.

9. The reactor system of claim 7, wherein the power source provides a plasma discharge that is a pulsed discharge.

10. The reactor system of claim 7, wherein at least one organic compound is injected with the liquid and the gas into the at least one electrically conductive inlet capillary tube electrode.

* * * * *